(12) United States Patent
Peeters et al.

(10) Patent No.: US 11,134,894 B2
(45) Date of Patent: Oct. 5, 2021

(54) DEVICE AND METHOD FOR MEASURING A PHYSIOLOGICAL PARAMETER OF A HUMAN LIMB

(71) Applicant: KONINKLIJKE PHILIPS N.V., Eindhoven (NL)

(72) Inventors: Wouter Herman Peeters, Waarle (NL); Sandra Liliana Ramirez Herrera, Eindhoven (NL); Ernest Roderick Laman, Waalre (NL); Ceren Bagatar, Eindhoven (NL); Pavankumar Murll Dadlani Mahtani, Eindhoven (NL); Suzanne Danielle Van Der Zaan-Landwehr Johan, Son en Breugel (NL); Eckhardt Henricus Matheus Schraven, Boxtel (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 348 days.

(21) Appl. No.: 16/315,681

(22) PCT Filed: Jul. 7, 2017

(86) PCT No.: PCT/EP2017/067108
§ 371 (c)(1),
(2) Date: Jan. 7, 2019

(87) PCT Pub. No.: WO2018/007593
PCT Pub. Date: Jan. 11, 2018

(65) Prior Publication Data
US 2019/0239809 A1   Aug. 8, 2019

(30) Foreign Application Priority Data
Jul. 8, 2016 (EP) ..................... 16178672

(51) Int. Cl.
*A61B 5/1455* (2006.01)
*A61B 5/00* (2006.01)
*A61B 5/024* (2006.01)

(52) U.S. Cl.
CPC ........ *A61B 5/6838* (2013.01); *A61B 5/02416* (2013.01); *A61B 5/14552* (2013.01); *A61B 5/6826* (2013.01); *A61B 2560/0443* (2013.01)

(58) Field of Classification Search
CPC .............. A61B 5/1455; A61B 5/14551; A61B 5/14552; A61B 5/6838; A61B 5/6826; A61B 2560/0443
See application file for complete search history.

(56) References Cited

U.S. PATENT DOCUMENTS

| | | |
|---|---|---|
| 5,035,243 A | 7/1991 | Muz |
| 6,154,667 A | 11/2000 | Miura |

(Continued)

FOREIGN PATENT DOCUMENTS

| | | |
|---|---|---|
| CN | 2500256 | 7/2002 |
| CN | 104287746 | 1/2015 |

(Continued)

OTHER PUBLICATIONS

Philips, "Reusable SpO2 sensors", 2009.
Covidien, "Respiratory Function Solutions, Sensor and Sampling Line Guide" 2013.

*Primary Examiner* — Eric F Winakur

(57) ABSTRACT

The present invention relates to a device for measuring a physiological parameter of a human limb such as peripheral capillary oxygen saturation. The device comprises a body comprising a first body part and a second body part, which are movable relative to each other to define an opening with an adjustable size for receiving the limb therein, and a physiological sensor for interacting with the limb received in the opening, the sensor being attached to the body, wherein (Continued)

the first and second body parts are slidable or twistable relative to each other while at least partially engaging or intersecting each other, or wherein the first and second body parts are configured to form a clip having an L-shaped end section for at least partially enclosing the limb received in the opening, in order to adjust the size of the opening.

12 Claims, 19 Drawing Sheets

(56) References Cited

U.S. PATENT DOCUMENTS

| | | | | |
|---|---|---|---|---|
| 6,606,512 B2* | 8/2003 | Muz | ............... | A61B 5/14552 |
| | | | | 600/322 |
| 6,654,621 B2* | 11/2003 | Palatnik | ............ | A61B 5/14552 |
| | | | | 600/322 |
| 8,145,288 B2* | 3/2012 | Baker, Jr. | .......... | A61B 5/14552 |
| | | | | 600/344 |
| 2010/0100007 A1 | 4/2010 | Sakamoto | | |
| 2010/0168531 A1 | 7/2010 | Shaltis | | |
| 2013/0131466 A1 | 5/2013 | Wacogne | | |

FOREIGN PATENT DOCUMENTS

| | | |
|---|---|---|
| FR | 2985656 | 7/2013 |
| JP | 2008067744 | 3/2008 |
| JP | 2009089818 | 4/2009 |
| WO | 2017009233 | 1/2017 |

* cited by examiner

DEVICE AND METHOD FOR MEASURING A PHYSIOLOGICAL PARAMETER OF A HUMAN LIMB

CROSS REFERENCE TO RELATED APPLICATIONS

This application is the U.S. National Phase application under 35 U.S.C. § 371 of International Application No. PCT/EP2017/067108, filed Jul. 7, 2017 published as WO 2018/007593 on Jan. 11, 2018, which claims the benefit of European Patent Application Number 16178672.8 filed Jul. 8, 2016. These applications are hereby incorporated by reference herein.

FIELD OF THE INVENTION

The present invention relates to a device and a method for measuring a physiological parameter of a human limb. In particular, the present invention relates to measuring the oxygen saturation in a non-invasive manner, especially by pulse oximetry on a limb of the human body by use of a pulse oximeter which illuminates the skin and measures changes in light absorption.

BACKGROUND OF THE INVENTION

Pulse oximetry is a technique to assess the peripheral capillary oxygen saturation ($SpO_2$) of blood in a non-invasive manner using an emitted and detected light signal. Typically, a red and infrared light signals are transmitted into the subject's finger by two light-emitting diodes (LEDs), and the scattered light is detected by a photodiode at the other side of the finger, where the blood oxygen saturation is derived from the ratio of pulse amplitudes in the red and infrared light intensity. Alternatively, the light can also be brought to the probe via one or more fibers, for instance one or more optical fibers. In this case, the light source is preferably the end of the fiber. There also may exist pulse oximeters using more than 2 wavelengths, in particular 3, 4, 5, 6, 7 or 8 wavelengths.

Although pulse oximetry is generally measured at the fingertip, other locations on the body are suitable (e.g. forehead, toe, ear lobe). Current probes suit adults' limbs in view of their size; infants, who have significantly smaller limbs, require tailored size probes. Different probes characterized by their sizes are currently on the market for infants such as to ensure not only comfort of the probe, but also to ensure the generation of a robust signal (e.g. measurement signal) of adequate quality and stability.

For example, U.S. Pat. No. 5,035,243 discloses a holder sleeve locking a detecting and measuring sensor into position, especially a detecting and measuring sensor for oximetric measurements, on the surface of a protruding part of a human body. The sensor includes a light source and a receiver which is sensitive to its radiation. The sleeve is elastically expandable and completely surrounds the body protruding part. Each of two diametrically opposite sections of the sleeve has a recess opening to the sleeve inside surface or is radiation-permeable to receive and hold the transmitter or the receiver. Both portions of the sleeve lying between these sections have pluralities of folds following one another around the sleeve periphery, with each fold forming a spring.

The major drawback of known probes is the problem of the different sizes in the limbs of infants of different age groups compared to the limbs of adults. The so-called "cloth peg mechanism" (clip around the limb) or the aforementioned sleeve are only suitable for a small range of infants and may easily be misplaced by untrained personnel, therefore leading to incorrect results. The sleeve-mechanism in the aforementioned U.S. patent document would allow a larger variety of limb sizes, but a major drawback of the sleeve mechanism is that placement cannot be done using one hand only. Another drawback of the sleeve mechanism is that the caregiver may be tempted to hold the limb while measuring, which leads to motion artifacts in the signal and inaccurate readings.

SUMMARY OF THE INVENTION

It is an object of the present invention to provide a device for measuring a physiological parameter of a human limb that will be suitable for humans of different age groups, in particular infants in the age range of 0-60 months, that allows accurate placement after installation.

In a first aspect of the present invention a device for measuring a physiological parameter of a human limb is provided that comprises a body comprising a first body part and a second body part, which are movable relative to each other to define an opening with an adjustable size for receiving the limb therein, and a receiving element for receiving a physiological sensor for interacting with the limb received in the opening, wherein, for the purpose of adjusting the size of the opening, the first and second body parts are slidable or twistable relative to each other while at least partially engaging or intersecting each other, or the first and second body parts are configured to form a clip having an L-shaped end section for at least partially enclosing the limb when received in the opening.

In a further aspect of the present invention, a method for measuring a physiological parameter of a human limb is provided that comprises the steps of providing a body comprising a first body part and a second body part, which are movable relative to each other to define an opening with an adjustable size for receiving the limb therein, receiving a sensor comprising a light source for generating a measurement light signal and a light detector for detecting the measurement light signal after its interaction with the limb received in the opening, and adjusting the size of the opening by sliding or twisting the first and second body parts relative to each other while they at least partially engage or intersect each other, or by configuring the first and second body parts to form a clip having an L-shaped end section for at least partially enclosing the limb when received in the opening.

Preferred embodiments of the invention are defined in the dependent claims. It shall be understood that the claimed method has similar and/or identical preferred embodiments as the claimed device and as defined in the dependent claims.

The present invention achieves an improved device for measuring a physiological parameter, in particular $SpO_2$ of blood, of a human limb which can be built with a plurality of alternative designs. The present invention is not restricted to measuring $SpO_2$, but can be applied to measuring other physiological parameters such as pulse rate, dyshaemoglobin fractions (e.g. carboxy-hemoglobin and methemoglobin), electrocardiogram, pulse arrival time and blood sugar. The present invention may be integrated in a pulse oximeter.

The receiving element may comprise, be coupled with or embed the physiological sensor, which preferably comprises a light source for generating a measurement light signal and a light detector for detecting the measurement light signal after its interaction.

By using a body with two body parts which are slidable relative to each other while at least partially engaging each other, the size of the opening defined by the two body parts can be adjusted by sliding one of the body parts along a length of the other one of the body parts while they are arranged to engage each other. In the engaging arrangement, one body part is at least partially within the other body part.

By using a body with two body parts which are twistable relative to each other while at least partially engaging each other, the size of the opening defined by the two body parts can be adjusted by twisting one of the body parts over an angle relative to the other one of the body parts while they are arranged to engage each other.

By using a body with two body parts which are slidable relative to each other while at least partially intersecting each other, the size of the opening defined by the two body parts can be adjusted by sliding one of the body parts along a length of the other one of the body parts while they are arranged to intersect each other. In the intersecting arrangement, an overlapping region where both body parts intersect or cross each other is within the respective body part when viewed essentially in a perpendicular direction to the cross-section of the opening along which the limb is to be received.

By using a body with two body parts which are twistable relative to each other while at least partially intersecting each other, the size of the opening defined by the two body parts can be adjusted by twisting one of the body parts over an angle relative to the other one of the body parts while they are arranged to intersect each other.

The above alternatives of the present invention is advantageous over the devices known from the prior art, especially from the aforementioned U.S. patent document. In particular, the size of the opening for receiving the limb is adjustable in an engaging or intersecting arrangement by sliding or twisting one body part relative to the other body part. In this way, the opening can be adjusted over a larger size range, using one hand only, whereas the device in the aforementioned U.S. patent document would require at least two hands to enlarge the opening. Also a disadvantage of the aforementioned U.S. patent document is that the opening will not be circular when the top and bottom parts are moved apart from each other, thereby complicating the insertion of the cylindrical-shaped body part. Preferably, the size can be adjusted from a minimum size where the two body parts are slid or twisted to just close the opening, to a maximum size where the two body parts are slid to just leave each other or are twisted to a maximum twisting angle.

In contrast, the device from the known device is not configured to change the size of the opening by sliding or twisting in an engaging or intersecting manner. In difference, the sleeve disclosed in the aforementioned U.S. patent document can be expanded between a minimum and a maximum size, thereby without any sliding or twisting of the two opposite sections in an engaging or intersecting manner.

Alternatively, by using a body with two body parts forming a clip having an L-shaped end section for at least partially enclosing the limb received in the opening, the size of the opening can be adjusted by moving the two body parts apart from each other, preferably in a twisting motion. The L-shaped end section, which can be arranged at either body part, advantageously prevents the received limb from erroneously slipping from the device. This renders the present invention more reliable compared to conventional devices having a clip as device body.

Preferably, the clip has a first opening and a second opening connected to and smaller than the first opening. The limb can be safely received by first stretching into the larger first opening and subsequently moving into the smaller second opening, thereby forcing the two body parts to move apart from each other. Further preferably, the first opening has a ring-shaped cross-section, which is advantageous for receiving cylinder-shaped body parts.

All above alternatives of the present invention achieve to enable accurate SpO2 measurements independent on the size of the limb, in particular for infants. The present invention therefore overcomes or at least reduces the draw-backs caused by unsatisfactory positioning of the device while attaching it to a patient, e.g. positioning the clip designed for being attached to a finger or toes to a different body part which is not optimal for $SpO_2$ measurements. The positioning of the limb relative to the device after being received in the opening is easier compared to known devices. The present invention also improves the alignment of the limb relative to the sensor optics resulting in more reliable $SpO_2$ measurements.

It is beneficial in that it facilitates correct placement of the device on both small and large limbs, thereby allowing the invention to be applied to a large age range. It is also beneficial in that it prevents misplacements on parts of the human body for which it is not mean to be used (for example a complete foot or an ear). Another benefit of the invention is that it allows being placed/attached to the body part that is to be measured with one hand only. A final benefit of the invention is that the caregiver will not be tempted to hold the limb while measuring, so that the measurement is less disturbed and the results are more reliable.

Preferably, the device according to the present invention is configured to form a circumventionally closed entrance by the opening, so that the safe receiving of cylinder-shaped body parts in the opening is improved. This also reduces the chance of erroneously attaching the device to receiving body parts with too large sizes or which are too broad for the device, such as a complete foot, a complete hand, a lip or an ear.

Preferably, the device further comprises a centering element for aligning the limb in the opening of the body relative to the receiving element. This enables to avoid erroneous positioning of the limb relative to the sensor optics, thereby leading to more reliable $SpO_2$ measurements.

Preferably, the centering element comprises a V-shaped section, preferably a V-shaped bottom section, formed in the first body part. This improves the contact between the bottom section of the first body part and the limb such as a finger, so that it can be safely positioned and received by the body parts, thereby improving the alignment of the received limb relative to the sensor optics.

Preferably, the centering element comprises a flexible material for filling up at least a part of a space between the limb received in the opening and a side of the opening. This provides the benefit to ensure contact between the limb and the device, in particular between the limb and a V- or U-shaped bottom of the device body, independent of the size of the limb, e.g. finger. This enables more reliable optical connection between the light source and the limb.

Preferably, the flexible material is configured to enclose at least a part of the sensor. Besides a more effective utilization of space, this also increases the stability of the relative position between the limb and the sensor optics, so that the $SpO_2$ measurements are more accurate.

Preferably, the centering element is provided by a connecting element arranged between the first and second body parts. This improves the alignment of the limb in the opening after it has been received. The connecting element may comprises an elastic sleeve, which further preferably have a predetermined shape so that the sleeve returns to the predetermined shape when no force is applied to the sleeve, and/or have a loop-like cross-section with a fully closed circumference.

Preferably, the centering element comprises a diaphragm, which is preferably attached to the first body part being an inner body part engagingly slidable along a length within the second body part being an outer body part. This enables reliable alignment of the limb received in the opening, leading to more accurate $SpO_2$ measurements.

Preferably, the centering element comprises two flexible membranes arranged adjacent to each other to define a slit within the opening. This enables a safe positioning of the limb after being received in the opening, leading to improved $SpO_2$ accuracy. Preferably, the first body part is an inner body part engagingly slidable along a length within the second body part being an outer body part. This enables to more reliably adjust the size of the opening for receiving the limb, since a sliding movement of the inner body part is easy to perform without exerting a large amount of force. Alternatively or additionally, the second body part comprises a blocking element for limiting the receivable depth of the limb. This prevents the limb, e.g. a finger from going completely through the opening of the device, thereby reducing the risk of entrapment of the limb.

The inner body part may comprise an inner tweezer part while the outer body part may comprise an outer tweezer part. The outer body part may comprise two holes on two opposite sides while the inner body part may comprise a single hole. The device can be configured by inserting an end of the inner body part into a recess provided on a first end of the outer body part and by sliding the inner body part towards a second end of the outer body part opposite to the first end. The opening is thereby formed by an overlap between the hole of the inner body part and the holes of the outer body part, wherein the overlap increases the further the inner body part is slid towards the second end of the outer body part. This enables a reliable adjustment of the size of the opening for receiving the limb, independent on the age group of patient or size of the limb.

Further preferably, a press surface of the inner body part for pressing the inner body part to slide within the outer body part is made of plastics or comprises protrusions spread over the surface to prevent slipping of the finger and ensure effective sliding. Additionally or alternatively, the surface may have a curved form with a bending towards the second end of the outer body part, when the inner body part is inserted into the recess of the outer body part, so that the sliding is easier.

Preferably, the opening comprises a circumference, wherein the first body part is arranged to intersect with the second body part over at least a part of the circumference of the opening. For instance, the two body parts may form a U-shaped opening with an end part being the overlapping region between the two body parts. Preferably, a loop-shaped band is fixated between the two body parts within the U-shaped opening. Another example is to configure the two body parts so that they both intersect and engage each other. In particular, the intersecting region and the engaging region are arranged at two opposite sides of the opening, while one or more additional intersecting regions may be provided between these two opposite sides.

Preferably, the second body part comprises two sliding holes for slidingly guiding the first body part, wherein two arms of the first body part are arranged to penetrate the sliding holes. This enables a device which is constructively easy and reliable in ensuring the correct positioning of the limb in the opening of the body parts. The second body part may have a flat form while the arms of the first body part may be straight or curved or made of a rigid/flexible/elastic material.

Preferably, the light source is connected to a surface of one of the first and second body parts and the light detector is connected to a surface of the other of the first and second body parts. This enables SpO2 measurements in transmission geometry where the light signal generated by the light source interacts with the limb by transmitting through it, or in a reflection geometry where the light signal generated by the light source interacts with the limb by being reflected on a surface of the latter. In the reflection geometry, the light source and the light detector may be located at the same side of the limb inside the opening. In particular, the light source and the light detector are separated from each other with a spacing of 2 to 10 mm, preferably of 3 to 7 mm. More preferably, the light reaching the light detector has been scattered inside the limb such that the light is backscattered into the direction of the light detector.

Preferably, the device further comprises a resetting element for charging the body parts with a resetting force in order to cause the body parts to be in a reset position relative to each other, and/or the sensor coupled to the body of the device. The resetting element is for instance a spring, an elastic sleeve or another elastic and/or form memory element, so that the two body parts are forced towards the reset position. Besides securely connecting the two body parts, this enables a reset size of the opening formed by the two body parts when these are in the reset position. Preferably, the resetting element comprises a spring connecting the first and second body parts, which is easy and cost-effective to provide. Another preferred resetting element is a pre-shaped piece of foam or silicone in contact with the stiff body parts. Having the sensor as an integrated part of the device body enables a compact device which can be used without being connected to external sensor optics, thus facilitating easy $SpO_2$ measurements.

Further preferably, the resetting element and the centering element may be configured as a single combined element fulfilling both functions of resetting and centering as described above. This embodiment enables easy fabrication and lower cost since an additional resetting element (e.g. a spring) is not necessary.

BRIEF DESCRIPTION OF THE DRAWINGS

These and other aspects of the invention will be apparent from and elucidated with reference to the embodiments described hereinafter. In the following drawings

FIG. 3B-2 shows the first embodiment with the second centering element shown in FIG. 3B-1;

FIGS. 6A-1 to 6A-5 and 6B-1 to 6B-2 show a fourth embodiment of a device according to the invention;

DETAILED DESCRIPTION OF THE INVENTION

Figure 1A:
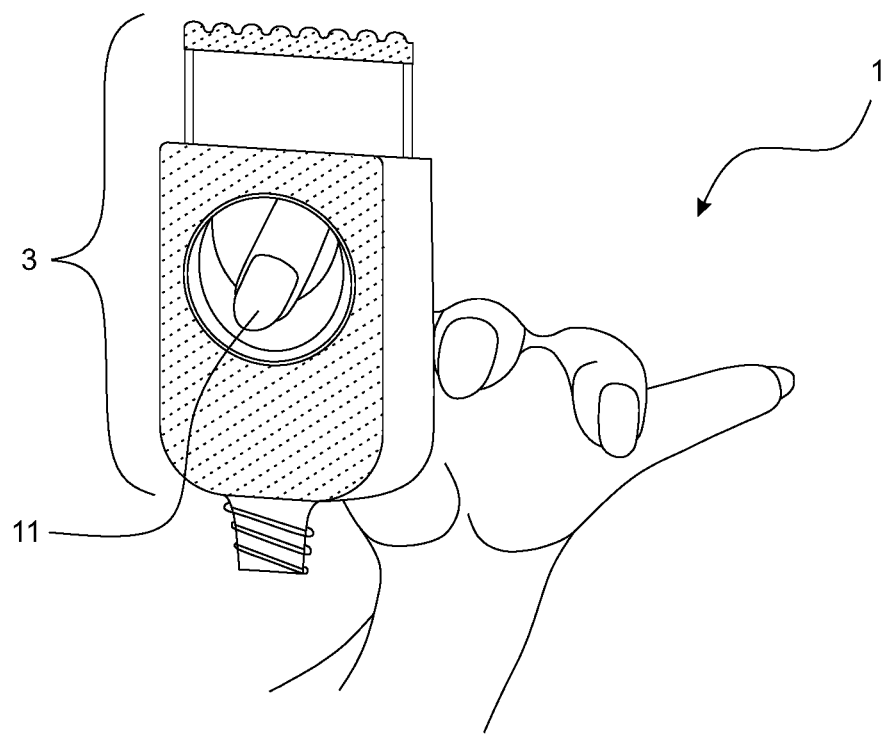
FIGS. 1A and 1B show a first embodiment of a device according to the invention in two different views.

Pulse oximetry is the technique to assess the oxygen saturation ($SpO_2$) of blood in a non-invasive manner. Since its introduction in the clinic in the 1980's, it has become a standard of care in various clinical settings. A pulse oximeter probe is usually applied to a fingertip. Red and infrared light is generated by a light source, for instance by two light-emitting diodes (LEDs), and transmitted into the tissue, and the scattered light is recorded by a light detector, for instance by a photodiode at the other side of the finger. The cardiac-induced pulsations in the blood volume manifest themselves as pulsations in the detected light intensity. The oxygen saturation is derived from the ratio of pulse amplitudes in the red and infrared light intensity, where the relationship results from a difference in color of oxygen-bound and oxygen-unbound hemoglobin.

The most ideal location to obtain a pulse oximetry signal is the fingertip or toe because the pulsatile optical signal is very strong on these locations, and the body site is easy to access. There are three types of mechanisms of attachment of pulse oximetry probes for fingers and toes. These probes operate preferably in a transmission geometry, where the detector and the source are at opposite sides of the finger.

For children, the size of the fingers and toes is significantly smaller compared to those of adults, so that special probes need to be designed to be suitable for these smaller sizes. For these designs it has not yet been realized to make a single clip that can fit on both large and small fingers and toes.

The major advantage of the so-called "cloth peg mechanism", also known as "finger clip", is that placement is intuitive and fixation occurs automatically upon release of the pulse oximeter. By compressing the handle, the clip opens up, the probe then needs to be placed over the finger or toe, and finally the handle only needs to be released for correct positioning. However, a disadvantage of the cloth peg mechanism is that it can easily be placed at the wrong body site. For example, one may try to position the finger clip of an adult on a complete foot of a neonate with the risk of wrong saturation values and wrong treatment of the patient.

Problems arising when designing a cloth-peg type of clip for fingers and toes for a larger age range of 0-60 months are mainly the possibility of positioning the clip on the wrong body part which becomes more dominant, because the fingers and toes are so small that the clinician may try to put the clip on for example the ear, hand palm or foot. Since the size of the finger/toe varies over a larger range (because of the large age range of the infants), the known clip design would be too large for the smallest finger or toe sizes. The alignment of the finger relative to the optics is prone to variation (i.e., incorrect placement) resulting in incorrect $SpO_2$ values. It becomes harder to correctly position the finger (or toe) between the light source and the light detector of the pulse oximeter, because the finger and toes can be very small, especially for premature infants.

The invention solves the above problems by providing a device with improved positioning of the limb in the opening formed by the two body parts.

Figure 1B:
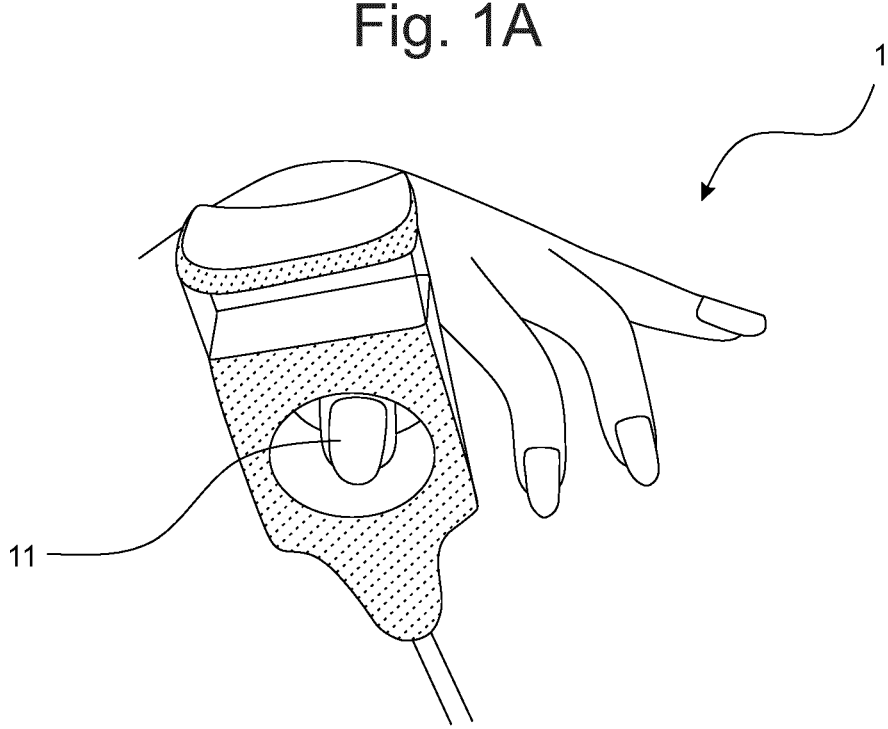
Figure 2A:
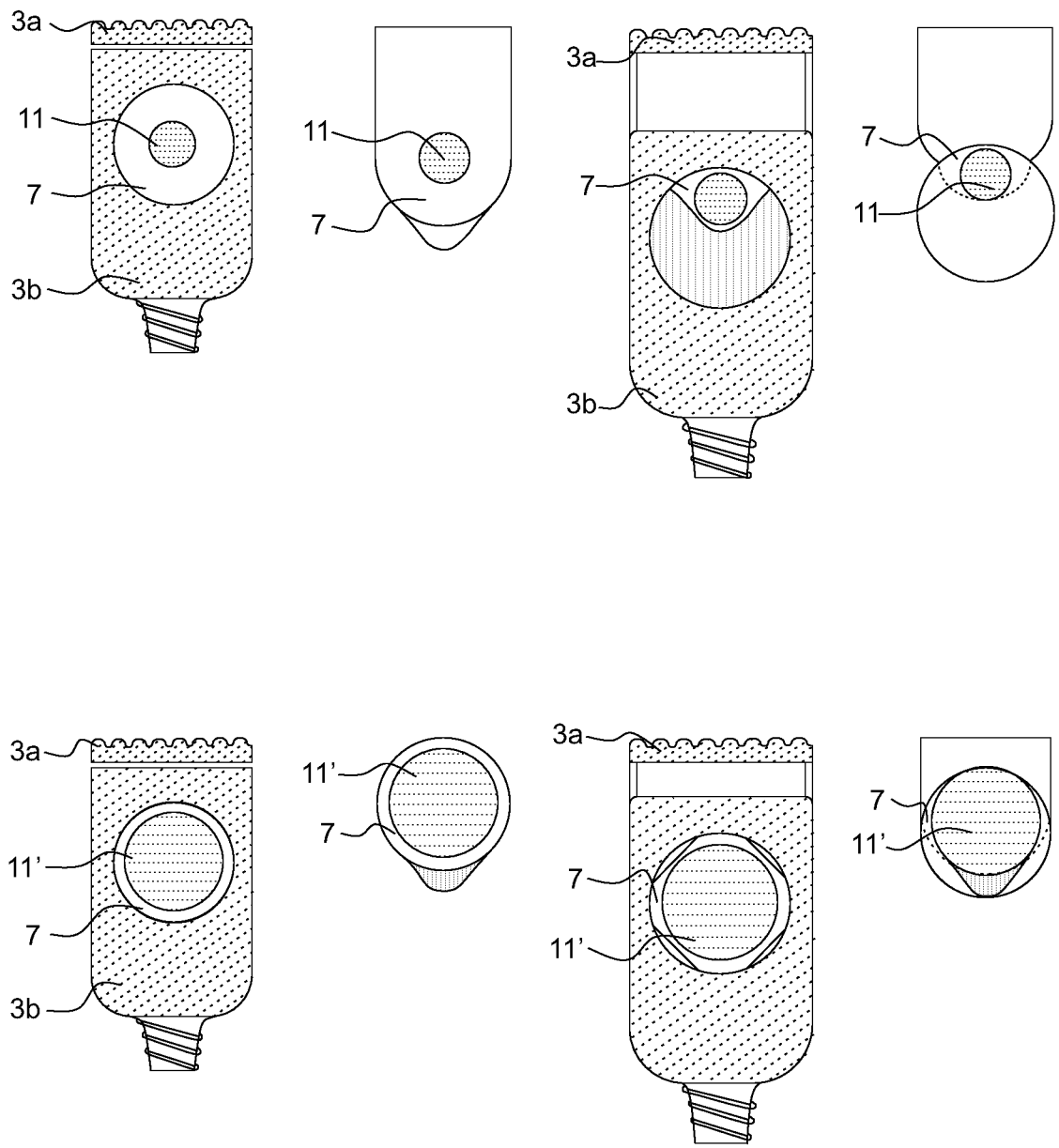
FIG. 2A shows the first embodiment wherein the opening is adjusted to various sizes.
Figure 2B:
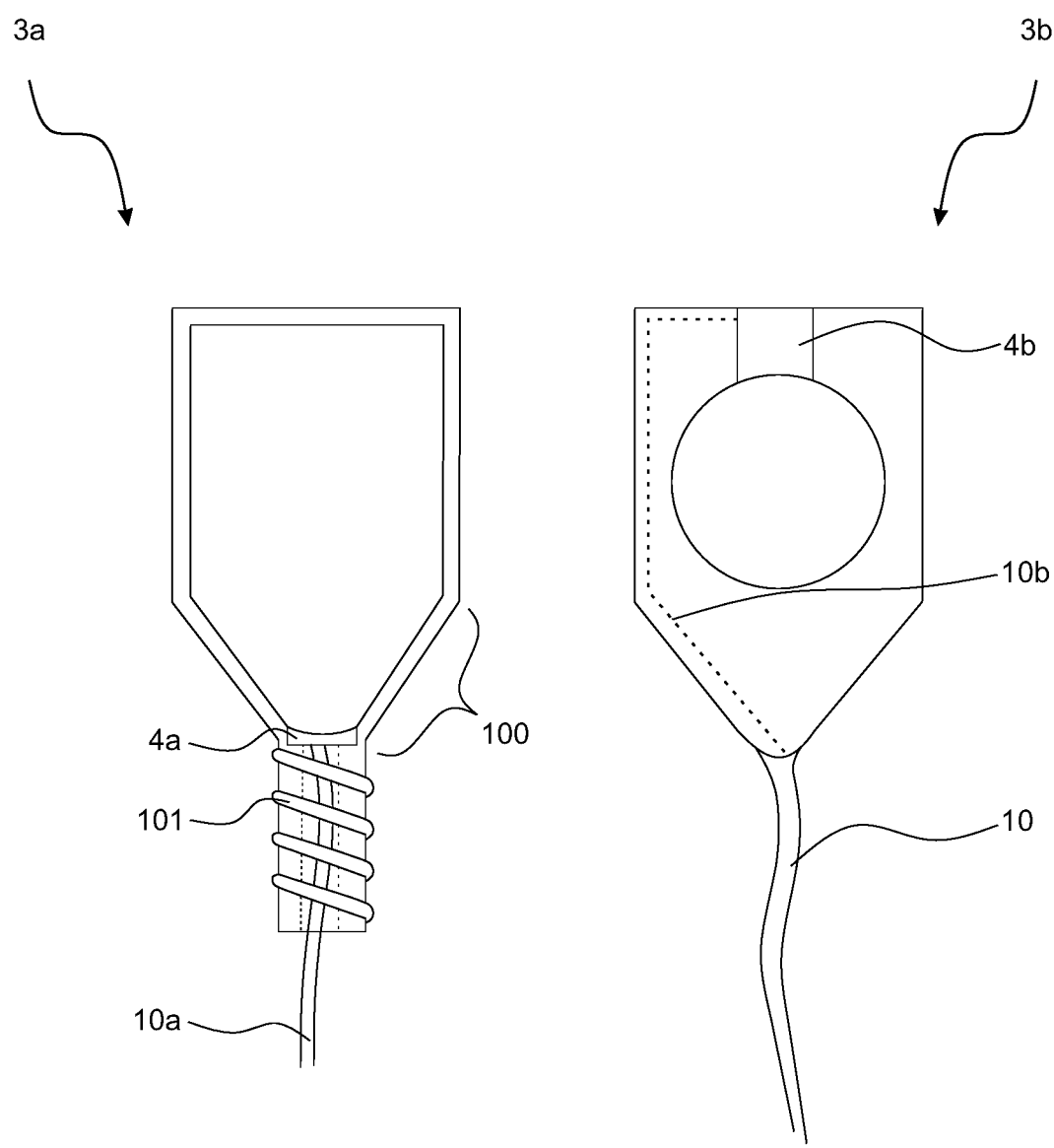
FIG. 2B shows the first body part and the second body part of the first embodiment.

FIGS. 1A and 1B show a first embodiment of a device 1 according to the invention in two different views. The device 1 comprises a body 3 for receiving a limb 11, such as a finger of a patient. The details of the device 1 are shown in FIGS. 2A and 2B.

Figure 3A:
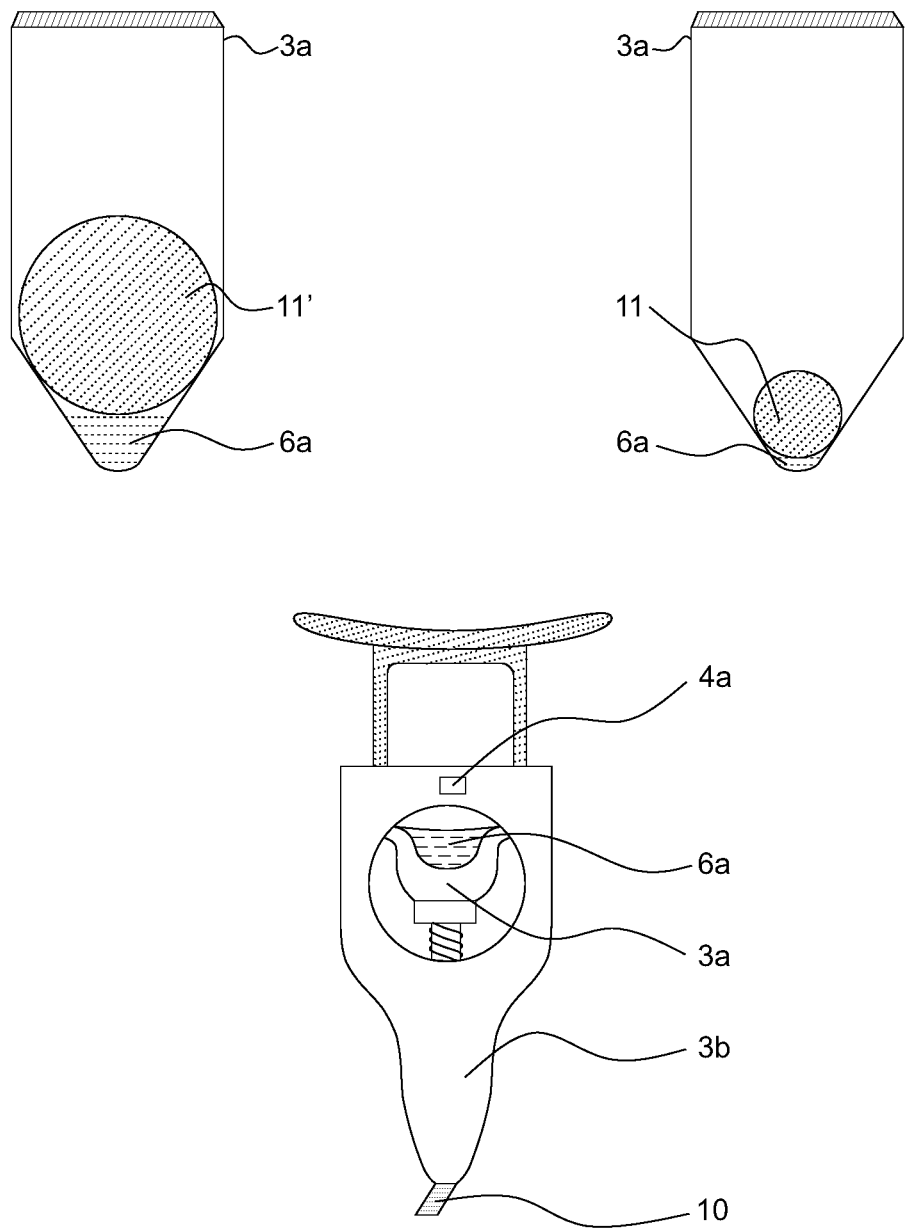
FIG. 3A shows the first embodiment with a first centering element.
Figures 1, 3B:
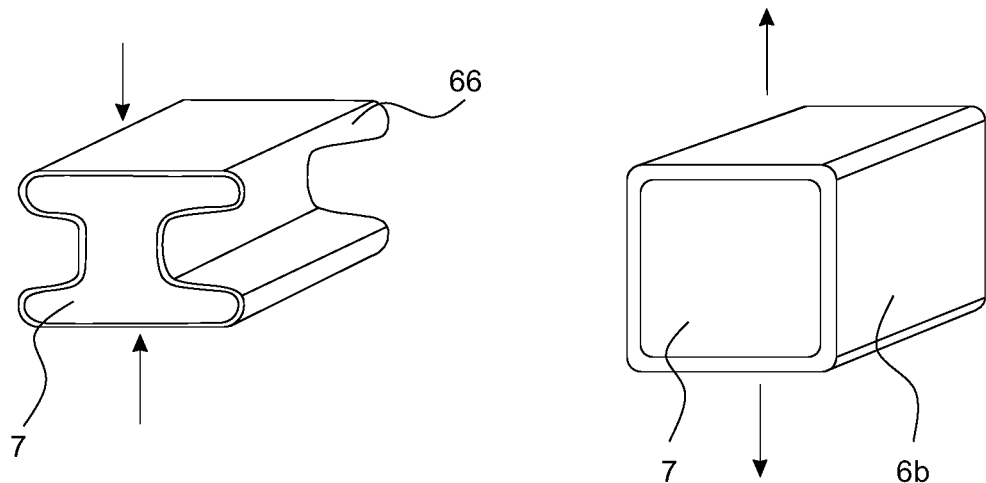
FIG. 3B-1 shows a second centering element.

As shown in FIG. 1, the device 1 has the appearance of a lace stopper, also known as "tanka". As shown in FIG. 2A, the body 3 of the device 1 consists of a first and a second body part 3a, 3b which are movable with respect to each other. In particular, the first body part 3a is an inner body part which can be inserted into the second body part 3b being an outer body part, so that the inner body part 3a can be slid along a length of the outer body part 3b.

Each body part 3a, 3b has one or two holes or apertures for entrance of the limb 11 such as finger or toe. The outer body part 3b has two apertures on opposite sides of the body part 3a, while the inner body part 3a has a single aperture 7b which passes throughout the thickness of the inner body part 3a ("all-through" aperture). The inner body part 3a is connected to the outer body part 3b via a resetting element 101. In the first embodiment, the resetting element 101 is a coil spring (FIG. 2B). The resetting element 101 charges the inner body part 3a with a resetting force, so that the inner and the outer body parts 3a, 3b return to a reset position relative to each other when no external force is applied to the body. In particular, the inner body part 3a is only partially inserted in the outer body part 3b when the body parts 3a, 3b are in the reset position.

The device 1 can be configured by inserting an end of the inner body part 3a into a recess provided on a first end of the outer body part 3b and by sliding the inner body part 3a towards a second end of the outer body part 3b opposite to the first end. The opening 7 for receiving the limb 11 is thereby formed by an overlap between the aperture of the inner body part 3a with the apertures of the outer body part 3b. The body 3 of the device 1 can be compressed by the operator, which effectively increases the overlap the further the inner body part 3a is slid towards the second end of the outer body part 3b.

In the left-most example shown in FIG. 2A, the inner body part 3a is slid into the outer body part 3b to its maximum insertion length, so that the size of the resulting opening 7 is maximum. The limb 11 can be placed into the opening 7. When the size of the limb 11 is smaller than the size of the opening 7, the inner body part 3a can be pushed towards the exterior of the outer body part 3b (in FIG. 2A upwards) until the limb 11 reaches simultaneously the top of the apertures of the outer body part 3b and the bottom of the aperture of the inner body part 3a. After releasing the compression force, the resetting element 101 pushes the inner body part 3a upwards so that the limb 11 becomes fixed and centered inside the device 1. In this way, the size of the opening 7 is adjusted to suit the limb 11.

In the left half of FIG. 2A, the limb 11 is exemplarily shown as a smaller finger. A similar adjustment can be performed to suit a larger finger 11', such as shown in the right half of FIG. 2A.

Preferably, a press surface of the inner body part 3a for pressing the inner body part to slide within the outer body part has a curved form with a bending towards the interior of the outer body part 3b as shown in FIG. 1B, thereby enabling easier application of compression force so that the insertion of the inner body part 3a into the outer body part 3b is easier.

A sensor 4a, 4b for the pulse oximetry measurement, which in the first embodiment is not a part of the device body 3, is coupled to the body 3 by a receiving element, e.g. a plug or an interface for data communication. The sensor can be oriented in transmission geometry or in reflection geometry. In transmission geometry shown in FIG. 2B, a light source 4a (e. g. LEDs) is located in the inner body part 3a, and a light detector 4b is integrated at the top side of the apertures in the outer body part 3b. In this way, the light source 4a and the light detector 4b are always aligned on opposing sides of the inserted limb 11. Furthermore, a cable 10b connecting the light detector 4b and the light source 4a as well as a cable 10a to a monitoring device (not shown in the figures) can be housed or embedded in the body 3 of the device 1, thus making the device 1 waterproof, and easy to clean. The cable 10a can further be guided inside the resetting element 101. Further, the cables 10a, 10b are preferably enclosed in an outer sheath 10 for improved protection and handling. The inner body part 3a comprises a V-shaped bottom section 100 for easily receiving the limb 11 and improved centering, i.e. aligning the limb 11 relative to the sensor optics, in particular the light source 4a and the light detector 4b. In reflection geometry, the sensor (4, 34, 44) also contains a light source (4a, 34a) and a light detector (4b, 34b), but the light source and the light detector are located at the same side of the limb inside the opening. Typically the light source and the light detector are separated from each other in between 2 and 10 mm, preferably 3-7 millimeters. The light that reached the light detector has been scattered inside the limb such the light is backscattered into the direction of the light detector.

For the first embodiment shown in FIGS. 1A-2B, there exist various methods to accomplish proper centering of the inserted limb 11. Centering is of vital importance to ensure the correct alignment of the limb 11 with respect to the light source 4a and the light detector 4b. By way of the centering, values of the oxygen saturation in the respective limb 11 can be collected in a very precise and especially in a repeatable way. The precision of the values is of outstanding importance to allow correct treatment and medication of the patient. Centering is accomplished by a centering element 6 as described in the following.

FIG. 3A shows the first embodiment with a first centering element comprising a V-shaped bottom section formed in the inner body part 3a. The aperture in the inner body part 3a is at least partially U- or V-shaped, preferably in a symmetric manner. Centering of the limb 11 is accomplished in an easy way by positioning the respective limb 11, 11' in the opening 7 and releasing the inner body part 3a. Due to the force of the resetting element 101, the inner body part 3a is moved outwards with respect to the outer body part 3b, thus diminishing the size of the resulting opening 7. The limb 11 is guided into the knee (i.e. the lowest point) of the U- or V-shaped bottom section of the inner body part 3a and thus centered with respect to the light source 4a which is preferably arranged in the knee of the inner body part 3a.

Optionally, as shown in FIG. 3A, a flexible or compressible material 6a can be added to fill up part of the V-shaped bottom section. This material 6a provides the benefit to ensure contact with the limb 11, 11', such as finger or toe, in the bottom section of the inner body part 3a, independently of the size of the finger or toe. This contact is needed for a reliable optical connection between the light source 4a and the limb 11, 11'. In the left first two examples of FIG. 3A, a very schematic view of an infant's finger 11' and of an adult's finger 11 is shown. The finger 11, 11' is inserted in the apertures and the inner body part 3a is released, thus reliably centering the limb. Preferably, the flexible material 6a is configured to enclose at least a part of the sensor 4. Besides a more effective utilization of space, this also increases the stability of the relative position between the limb 11, 11' and the sensor optics, so that the SpO$_2$ measurements are more accurate.

FIG. 3A explains in detail the benefit of the flexible material 6a. Especially in the case of a large finger 11', it is not likely for it to reach the lowest part of the inner body part 3a. The flexible material 6a will fill up the space between the finger 11, 11' and the bottom side of the inner body part 3a so as to ensure a sufficient contact between the finger 11,11' and the sensor 4. Combining the V-shaped bottom section 100 of the inner body part 3a with the flexible material 6a allows the finger 11, 11' to sink deeply into the bottom section 100, thereby providing optimal centering.

Alternatively, the centering of the limb 11 can be achieved by using a connecting element, which may comprise an elastic sleeve 6b as shown in FIG. 3B-1. Preferably, the elastic sleeve has a predetermined shape to which the sleeve 6b returns after being deformed when no external force is applied to the sleeve 6b. Further preferably, the sleeve 6b has a loop-like cross-section with a fully closed circumference defining the opening 7 for receiving the limb 11.

Figures 2, 3B:
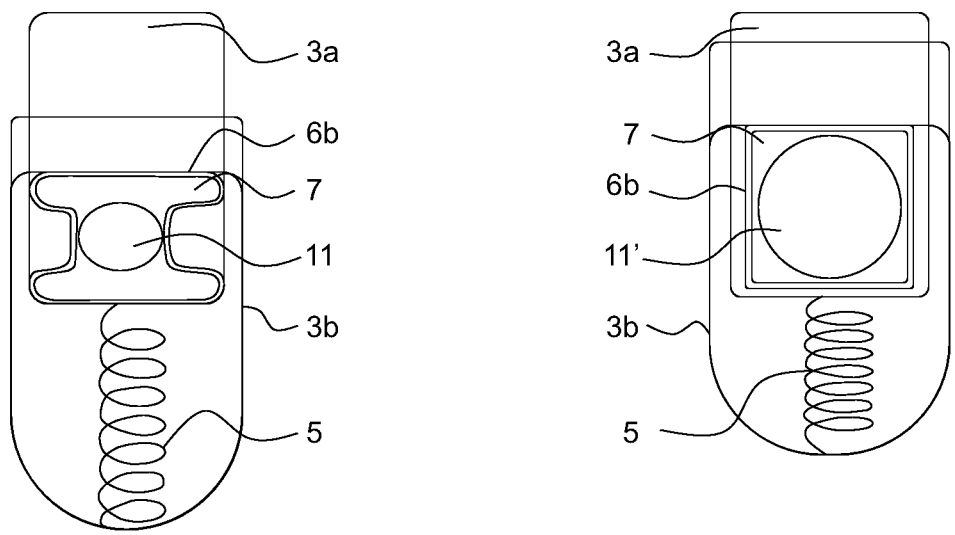

FIG. 3B-2 shows how the elastic sleeve 6b, preferably a pre-shaped semi-flexible band, can be incorporated in the lace-stopper design. In particular, the two body parts 3a, 3b are connected via two sides of the flexible sleeve 6b. The top side of the sleeve 6b is connected to the top side of the outer body part 3b while bottom side of the sleeve 6b is connected to the bottom side of the inner body part 3b. The flexible sleeve 6b is pre-shaped such that in the unconstrained form, the sidewalls of the sleeve 6b bend inwardly. Such an elastic sleeve 6b is suitable for use when receiving a small finger 11 (left example of FIG. 3B-2) and a large finger 11' (right example of FIG. 3B-2).

Figure 3C:
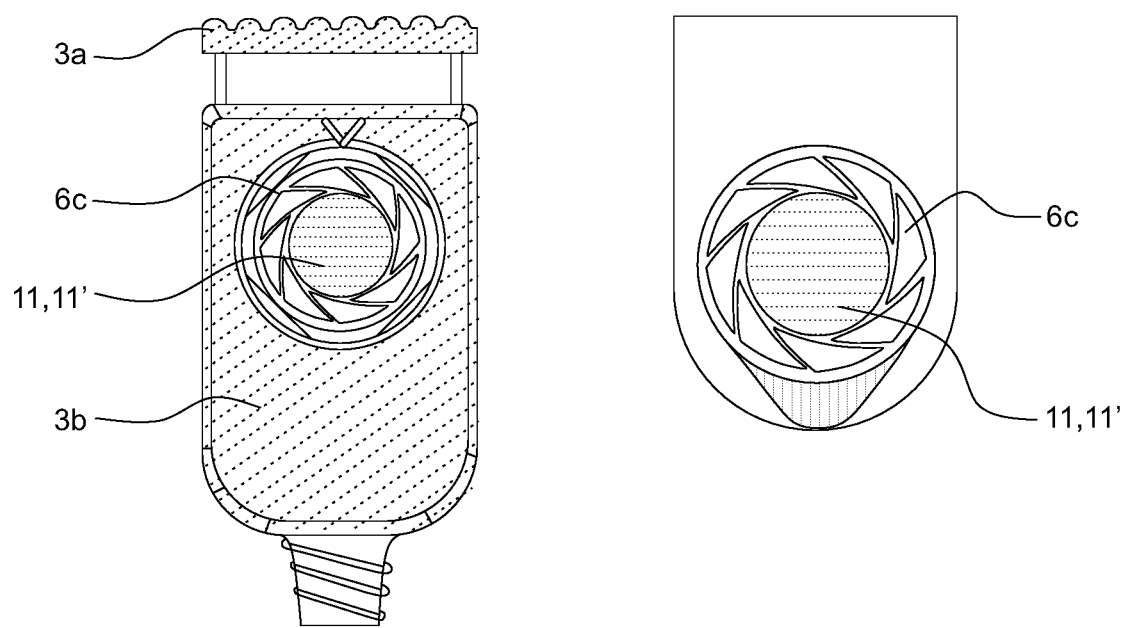
FIG. 3C shows the first embodiment with a third centering element.

FIG. 3C shows the first embodiment with a third centering element. Preferably, the centering element comprises a diaphragm 6c, which is preferably attached to the inner body part 3a. This enables reliable alignment of the limb 11, 11' received in the opening 7, leading to more accurate SpO$_2$ measurements.

Figure 3D:
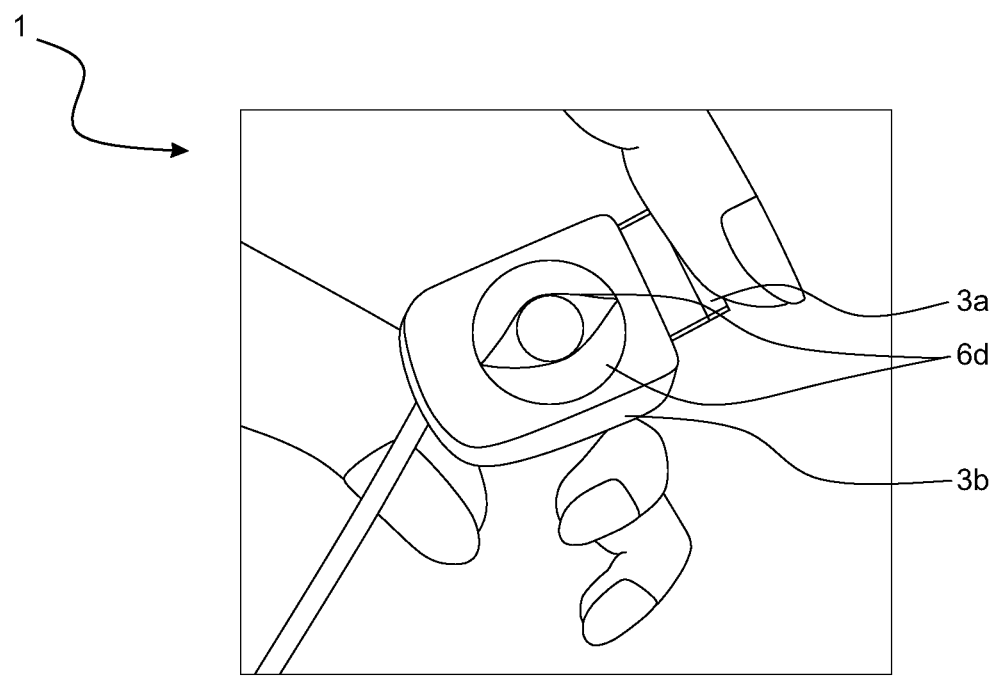
FIG. 3D shows the first embodiment with a fourth centering element.

FIG. 3D shows the first embodiment with a fourth centering element. Preferably, the centering element comprises two flexible membranes 6d arranged adjacent to each other to define a slit within the opening 7. Further preferably, the slit is oriented along the direction in which the limb 11, 11' is to be received. This enables a safe positioning of the limb after being received in the opening 7, leading to improved SpO$_2$ accuracy. Further preferably, a first person such as caregiver is able to hold the device body 3a, 3b while the device can be placed onto a limb such as a finger of a patient by guiding the finger into the slit of the flexible membranes 6d.

Figure 4A:
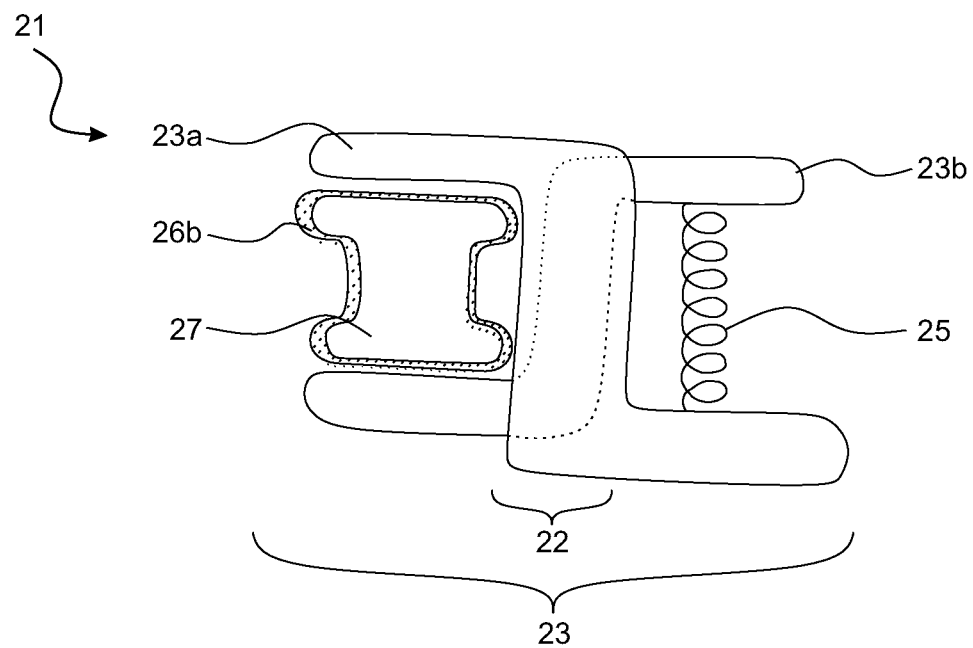
FIGS. 4A and 4B show a second embodiment of a device according to the invention.
Figure 4B:
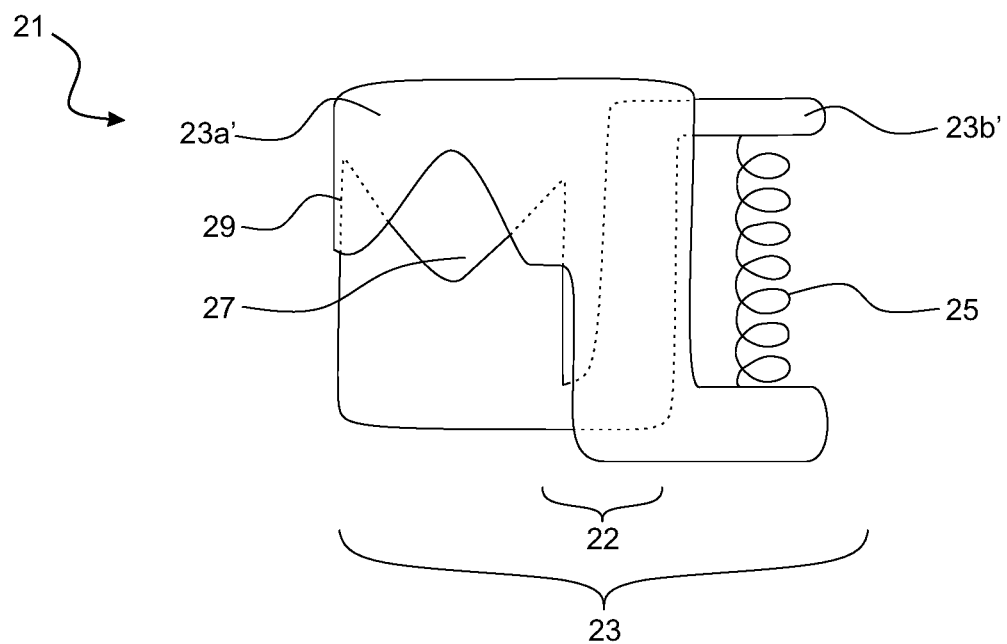

FIG. 4A, 4B shows a second embodiment of a device 21, 21' according to the invention.

The two body parts are exemplarily configured as tweezer elements 23a, 23b or 23a', 23b' of a clip whose handle sides are connected by a spring 25, wherein the first and second tweezer elements 23a, 23b or 23a', 23b' move with respect to each other via a sliding mechanism. The spring 25 exerts a force which pushes the handle sides of the tweezer elements 23a,23b or 23a',23b' apart such that the tweezer sides of the tweezer elements 23a,23b or 23a',23b', which are opposite to the handle sides, tend to move closer to each other, thereby providing a natural clamping force.

The opening 27 for the limb 11 is provided by either a flexible loop-shaped band 26b that is fixated between the tweezer elements 23a, 23b (FIG. 4A), or by shaping the tweezer elements 23a',23b' such that they grab into each other in at least one region 29 (FIG. 4B). Preferably, the first tweezer element 23a' is configured to enclose the second tweezer element 23b' in the region 29.

Preferably, the first tweezer element 23a, 23a' is arranged to intersect with the second tweezer element 23b, 23b' while overlapping in a region 22 of the circumference of the opening 27. For instance, the two tweezer elements may form a U-shaped opening with an end part being the overlapping region 22 between the two body parts, as shown in FIG. 4. Preferably, the loop-shaped band 26b is fixated between the two tweezer elements 23a, 23b within the U-shaped opening.

Another example is to configure the two tweezer elements 23a', 23b' so that they both intersect and engage each other, as shown in FIG. 4B. In particular, the intersecting region 22 and the engaging region 29 are arranged at two opposite sides of the opening, while one or more additional intersecting regions may be provided between these two opposite sides. Centering of the finger is achieved by a V-shaped bottom section of one or both of the body parts (FIG. 4) or the loop-shaped band (FIG. 5).

In FIG. 4, the two tweezer elements 23a,23b or 23a',23b' are slidable relative to each other while engaging and/or intersecting each other, in order to adjust the size of the opening 27 for receiving the limb 11. Alternatively or additionally, the two tweezer elements may be twistable relative to each other while engaging and/or intersecting each other, in order to adjust the size of the opening. In particular, the tweezer elements may move with respect to one another via a hinge, thus making an angular displacement with respect to one another.

Another method of creating an opening for receiving the limb is by molding the clip-shaped device 21 into a flexible silicone jacket that has such morphology that an opening exists between the two tweezer elements. This silicone jacket would protect the interior from collecting dirt like sand, body fluids, or dust. This protection increases the life-time of the sliding mechanism, and it also facilitates cleaning of the device. One can easily hold the device under tap water and no fluid would enter the interior of the clip.

Figure 5A:
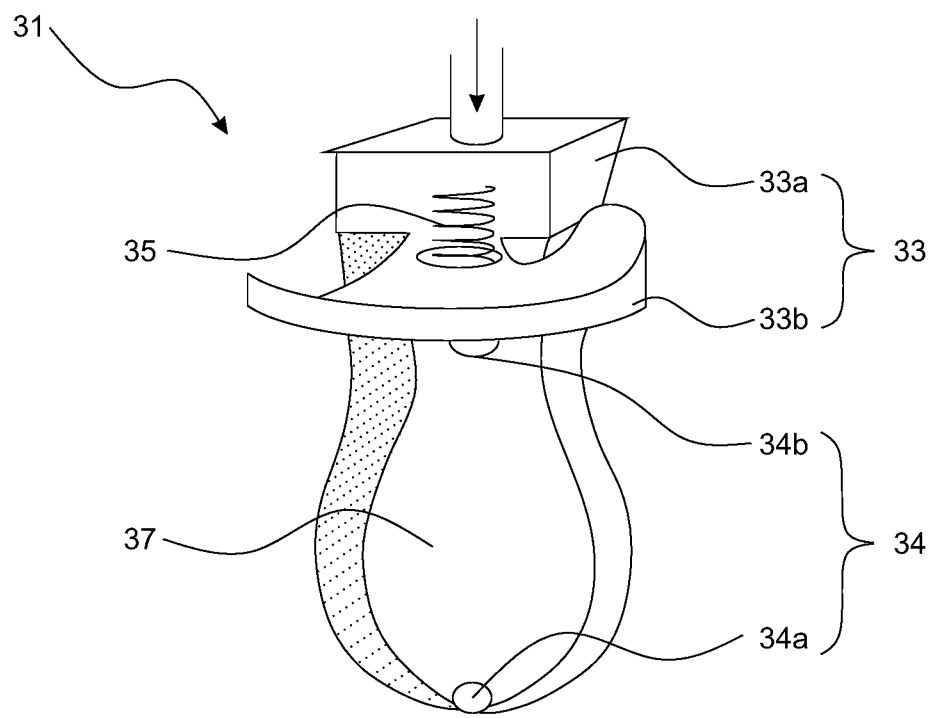
FIGS. 5A to 5E show a third embodiment of a device according to the invention.

FIG. 5A shows a third embodiment of a device 31 according to the invention.

Preferably, the second body part 33b comprises two sliding holes for slidingly guiding the first body part 33a. The first body part 33a comprises two arms fixated to a main body of the first body part 33a, wherein the two arms are arranged to penetrate the sliding holes. This enables a device which is constructively easy and reliable in ensuring the correct positioning of the limb 11 in the opening 37 of the body parts 33a, 33b (FIG. 5E). The second body part 33b may have a flat or slightly pre-shaped form as shown in FIG. 5A while the arms of the first body part 33a may be made of a flexible or elastic band.

Figure 5B:
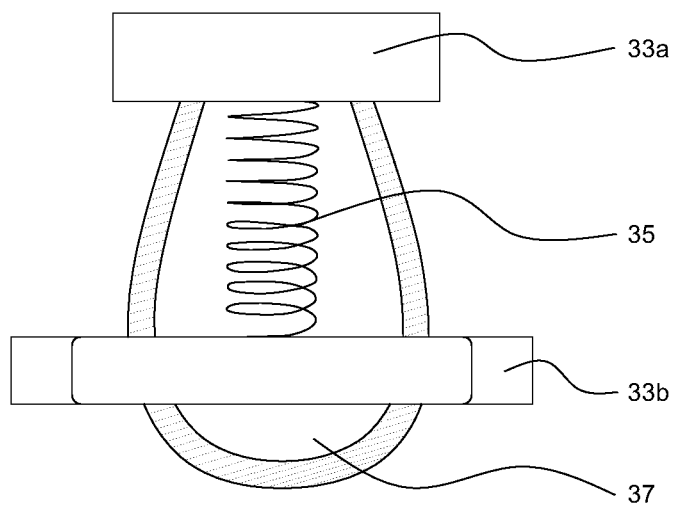

A resetting element, for example a spring 35 as seen in FIG. 5B, is placed in between the first and the second body part 33a, 33b. Preferably, the spring 35 is arranged between a lower side of the main body of the first body part 33a and an upper side of the flat form of the second body part 33b. The light source 34a is arranged at the bottom of the flexible band facing the light detector 34b arranged at a lower side of the flat form of the second body part 33b. Alternatively, also the light source 34a is located at the top part next to the light detector 34b, such that the measurement is performed in reflection geometry.

Figure 5C:
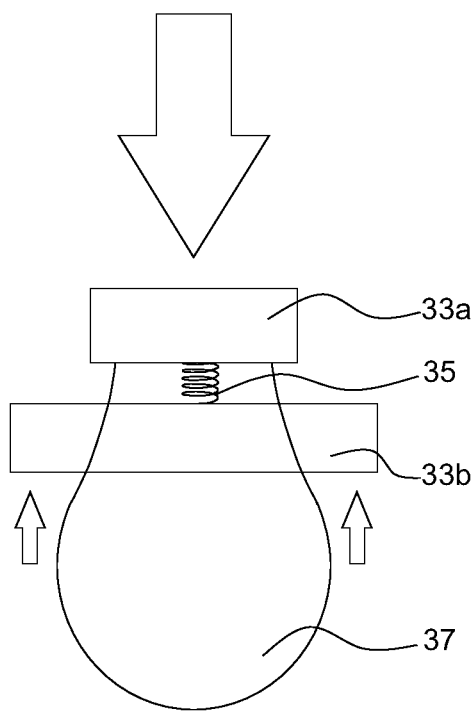
Figure 5D:
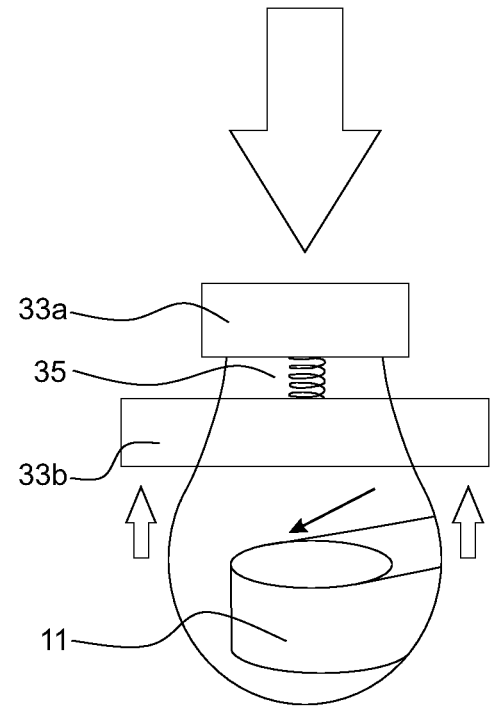
Figure 5E:
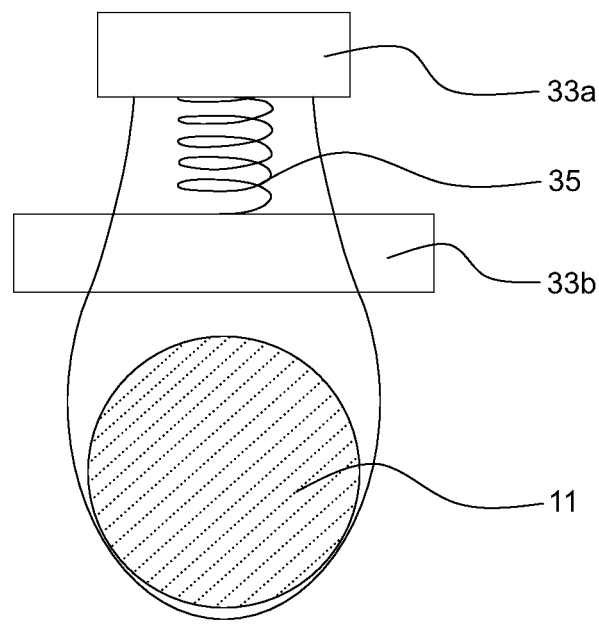

In the reset position of the body parts 33a, 33b as shown in FIG. 5C, the two body parts 33a, 33b are pulled apart by the force of the spring 37. The opening 37 created in between the first and the second body part 33a, 33b can be enlarged by compressing the spring 35 (indicated by the arrows in FIGS. 5C-D), such that the first body part 33a slides through the second body part 33b. In this way, the opening 37 can accommodate both smaller and larger fingers and toes.

FIGS. 6A-1 to 6A-5 and 6B-1 to 6B-2 show a fourth embodiment of a device 41 according to the invention.

The body 43 of the device 41 is formed as a clip where the two body parts 43a, 43b are integrated as one single part. An L-shaped end section 43d is provided at the body 43, here at the second body part 43b, for at least partially enclosing the limb 11 received in the opening 47. The size of the opening 47 can be adjusted by moving the two body parts 43a, 43b apart from each other, preferably in a twisting motion around an axis at the top of a ring section 43c of the body 43. The L-shaped end section 43d, which can be arranged at either body part 43a, 43b, advantageously prevents the received limb 11 from erroneously slipping from the device 41. This renders the present invention more reliable compared to conventional devices having a clip as device body.

Preferably, the clip has a first opening 49 and a second opening 47 connected to and smaller than the first opening 49. The limb 11 can be safely received by first stretching into the larger first opening 49 and subsequently moving into the smaller second opening 47, thereby forcing the two body parts 43a, 43b to move apart from each other. This last (downward) movement is indicated by the arrow shown in the second example from the left in FIG. 6A. Further preferably, the first opening 49 has a ring-shaped cross-section, which is advantageous for receiving cylinder-shaped body parts.

Figures 1, 6A:
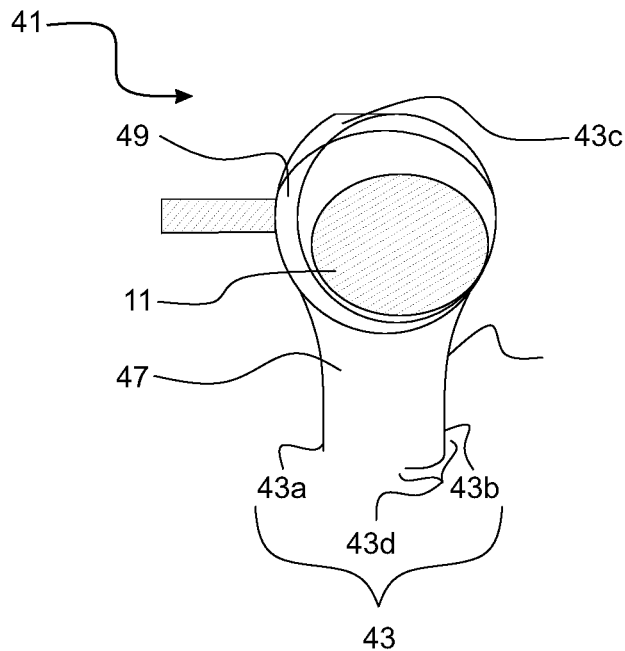
Figures 2, 6A:
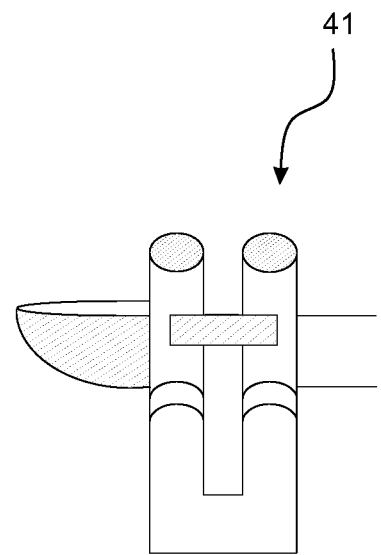
Figures 3, 6A:
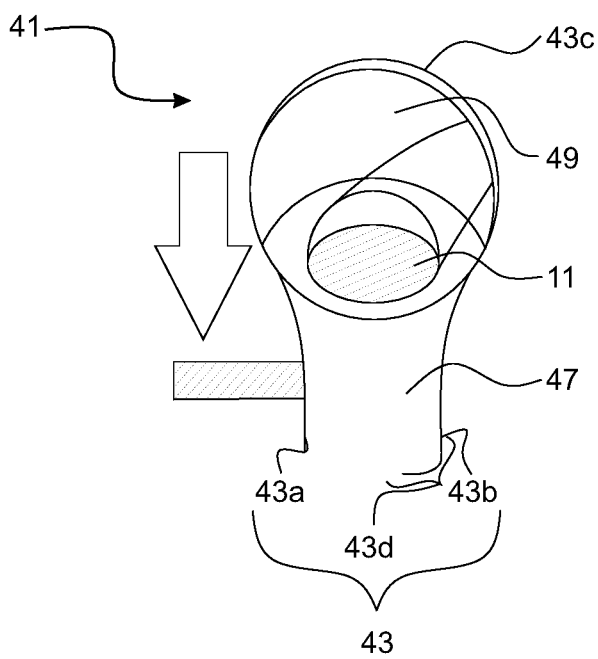
Figures 4, 6A:
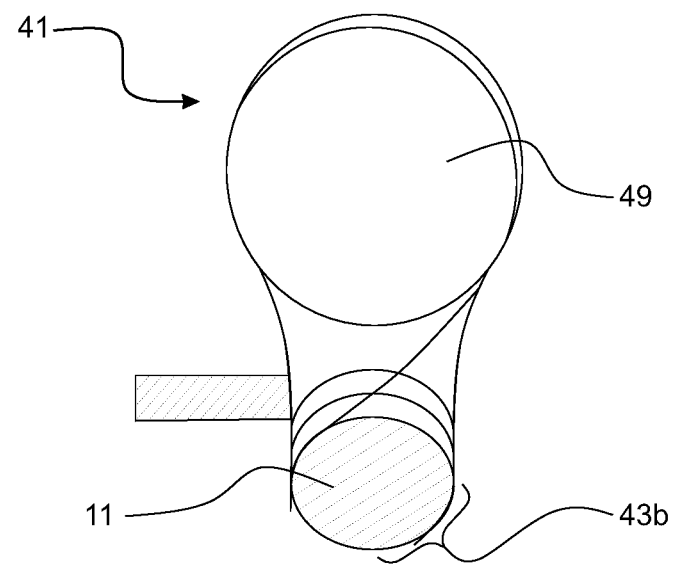
Figures 5, 6A:
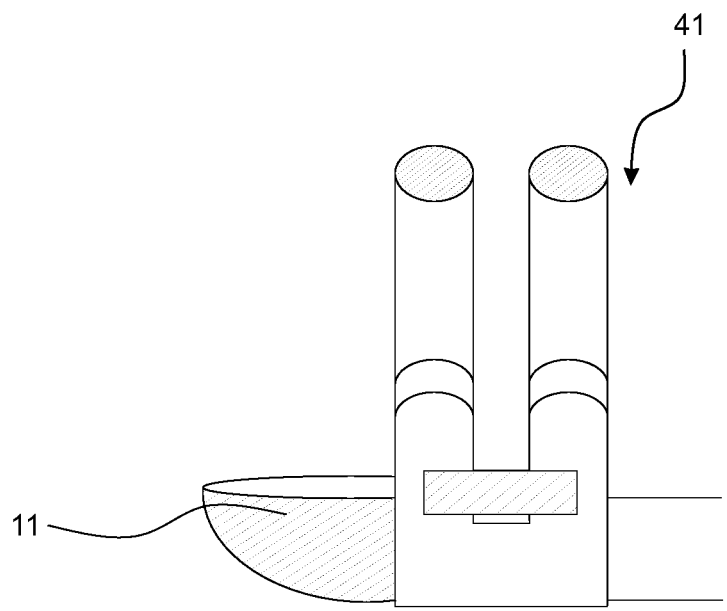
Figures 1, 6B:
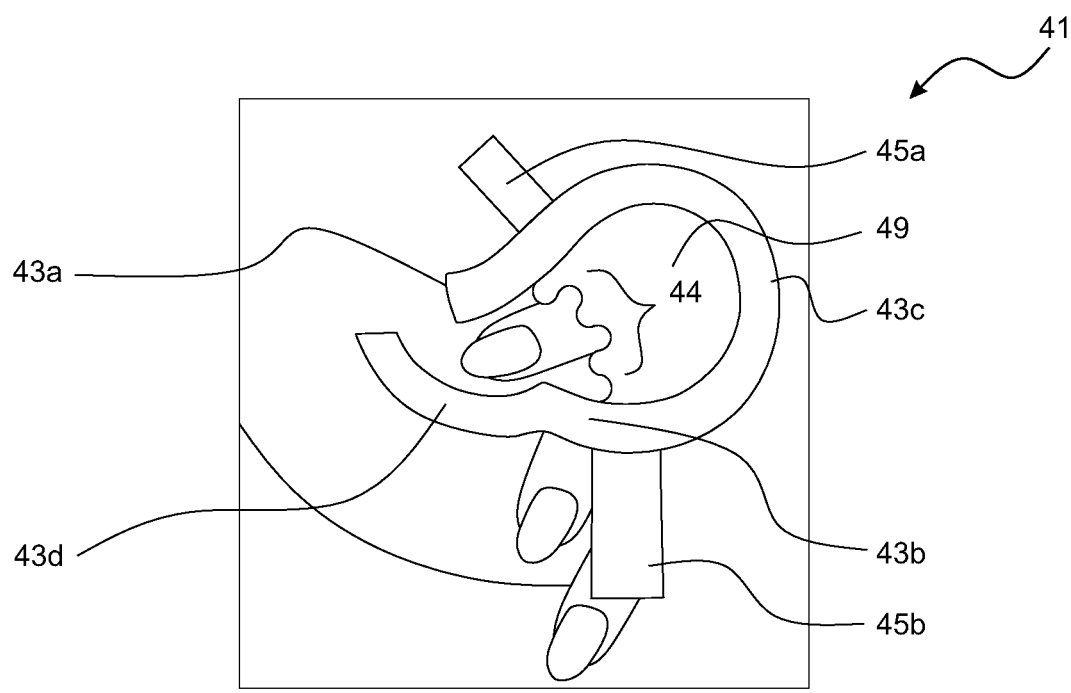
Figures 2, 6B:
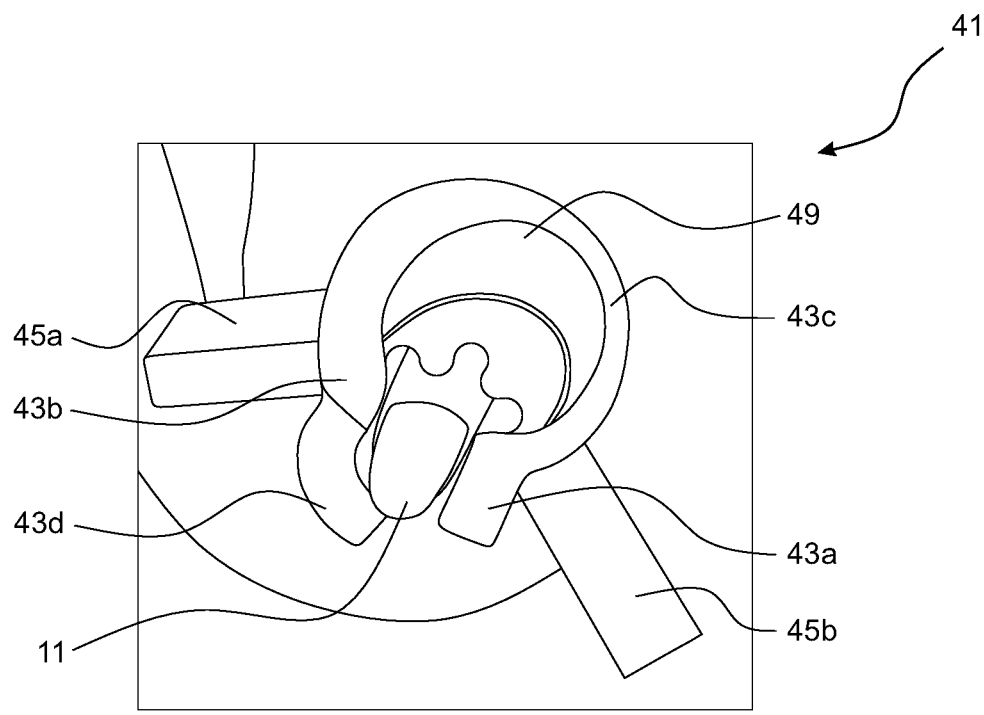

As shown in the FIG. 6A-3, if the lever (shown as shaded area under the arrow) is pulled or pushed down as indicated by the arrow, the finger 11 is preferably positioned in the space between the arms 43a and 43b. This is also the case in the situation shown in FIG. 6A-4.

Further preferably, the device 41 comprises an "omega-shaped" body 43 formed by a semi-flexible loop (shown in FIGS. 6B-1 and 6B-2) where the sensor optics 44, e.g. for the $SpO_2$ and/or photoplethysmography (PPG) measurement, is embedded in between the two body parts 43a, 43b of the omega-shaped body 43 formed as arms.

Preferably, the device 41 enables the patient being investigated to place his finger 11 so that the tip of the finger 11 is stretched out straightly, as shown in FIG. 6A-5.

When attaching the device 41 to the limb 11 such as finger or toe, the finger 11 is first placed inside the first opening 49 of the omega-shaped body 43 and subsequently pushed downwards in between the arms 43a, 43b of the omega-shaped body 43. One of the arms 43a, 43b comprises the L-shaped end section 43d to prevent the finger or toe from escaping through the bottom of the omega-shaped body 43.

A handle 45a, b may be provided at the body 43 that, if operated by the caregiver, pushes the finger or toe downwards into the space in between the two arms 43a, 43b of the omega-shaped body 43. The handle 45a, b preferably slides through body part 43c, which has a front face and a rear face in between which the handle can slide. The handle 45a, b may also be connected to body part 43c via a hinge. In both cases the handle needs to be operated by the caregiver, who needs to push the handle down to position the limp in between 43a and 43b.

FIGS. 7A-D show a fifth embodiment of a device 51 according to the invention.

Figure 7A:
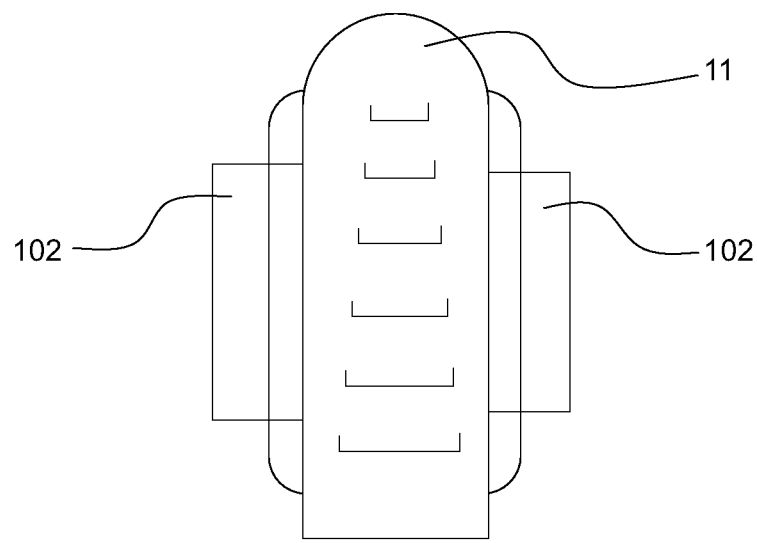
FIGS. 7A to 7D show a fifth embodiment of a device according to the invention.
Figure 7B:
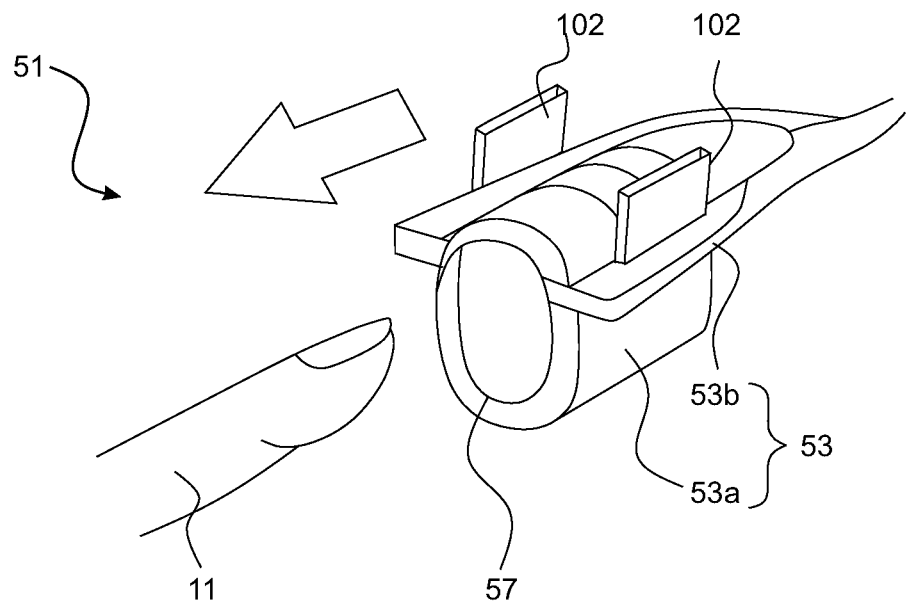
Figure 7C:
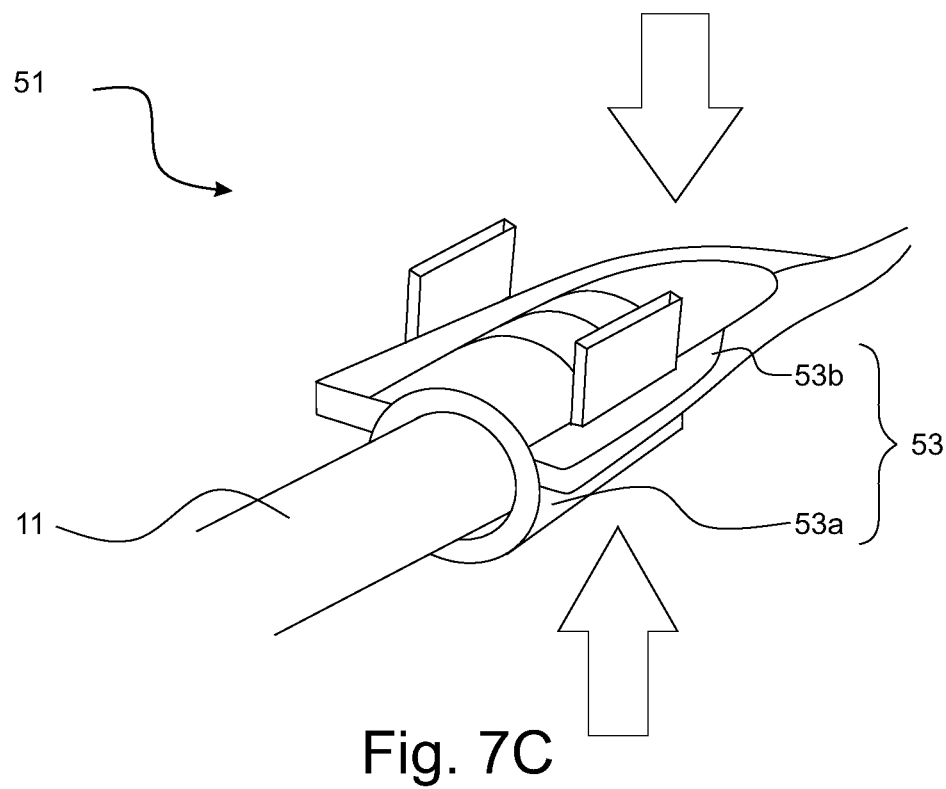
Figure 7D:
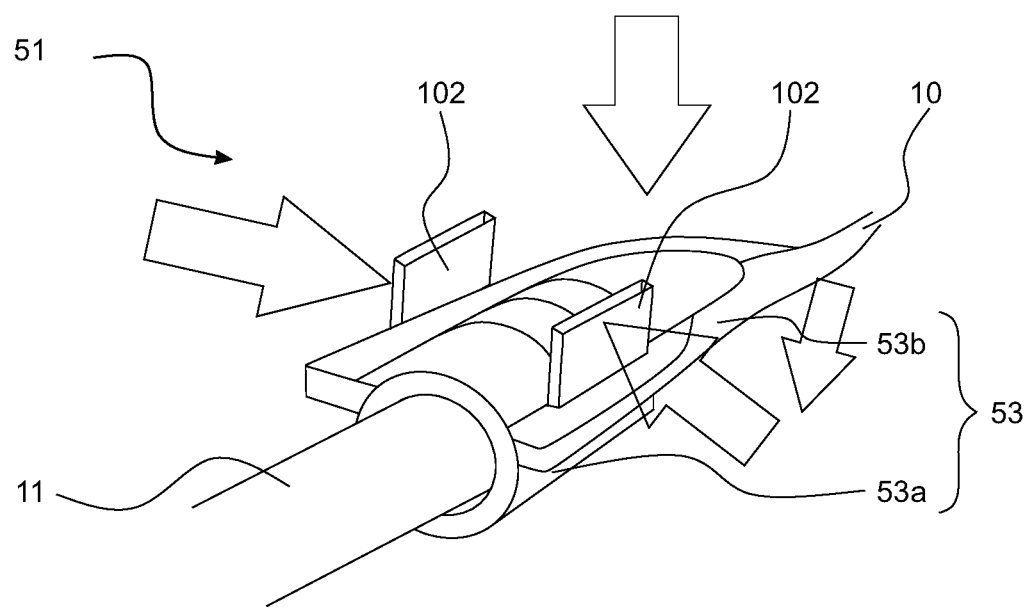

The body 53 of the device 51 shown in FIG. 7B is similar to the device 31 shown in FIG. 5, with a difference that the first body part 53a in FIG. 7B is not formed as a flat main body with a flexible band, but a rigid part having a curved section and two arms 102 for penetrating two holes of the second body part 53b (see also FIG. 7A). The sheath 10 enclosing the cables 10a, 10b (analog to FIG. 2B) are formed as an extension of the second body part 53b.

In FIG. 7B, the device 51 is placed over the limb 11 being a finger (indicated by the arrow). The two body parts 53a, 53b can move with respect to one another such that the spacing between them and thus the size of the opening 57 for receiving the limb 11 can be varied. After the device 51 is placed over the limb 11, the fixation of the limb 11 within the opening 57 can be improved by pushing the two body parts 53a, 53b closer to each other (indicated by the arrows in FIGS. 7B-C). In particular, the two arms 102 of the first body part 53a can be pushed horizontally towards each other to strengthen the fixation of the finger 11 in the opening 57.

The contact areas between the two body parts 53a, 53b are configured so that some degree of friction exists at the contact interfaces. For instance, a plurality of rims may be provided at the interfaces so that the two body parts 53a, 53b cannot easily be pushed apart from each other by the finger or toe leading to higher safety of positioning and centering.

Figure 8A:
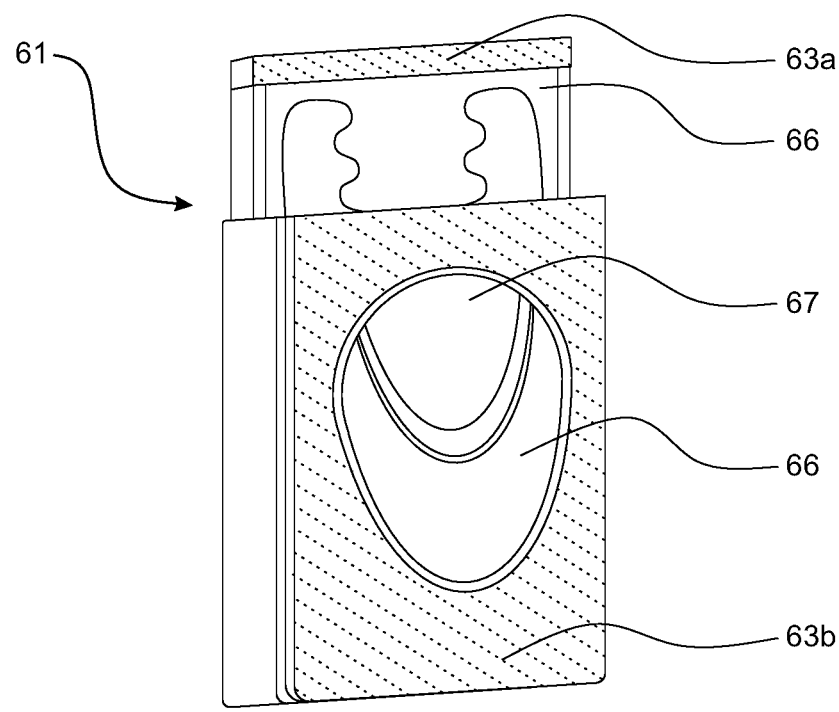
FIGS. 8A and 8B show a sixth embodiment of a device according to the invention.

FIG. 8 shows a sixth embodiment of the device 61 according to the present invention. The device comprises a body having a first body part 63a being an inner body part and a second body part 63b being an outer body part, such that the inner body part is slidable within the outer body part while the two body parts engage each other. FIG. 8A shows a front view of the device 61 where a hole is arranged on a front surface of the outer body part 63b and the inner body part 63a, respectively. In the engaged state shown in FIG. 8A, an opening 67 for receiving a limb (e.g. a finger) is formed as overlap between the two holes of the body parts 63a, b.

A piece of elastic foam 66 is provided as an element to fill partially the space between the inner and the outer body parts 63a, b. Due to the elasticity of the foam 66, it also serves as a resetting element. In this way, the elastic foam 66 is able to exert an elastic force to the inner body part 63a so that it stretches out of the outer body part 63b. By pressing down the inner body part 63a towards the interior of the outer body part 63b, the opening 66 can be enlarged and adjusted in its size. Alternatively, a piece of flexible silicon may be used instead of or in addition to the foam 66. In a preferable embodiment, the foam 66 serves as resetting element but not as centering element.

Figure 8B:
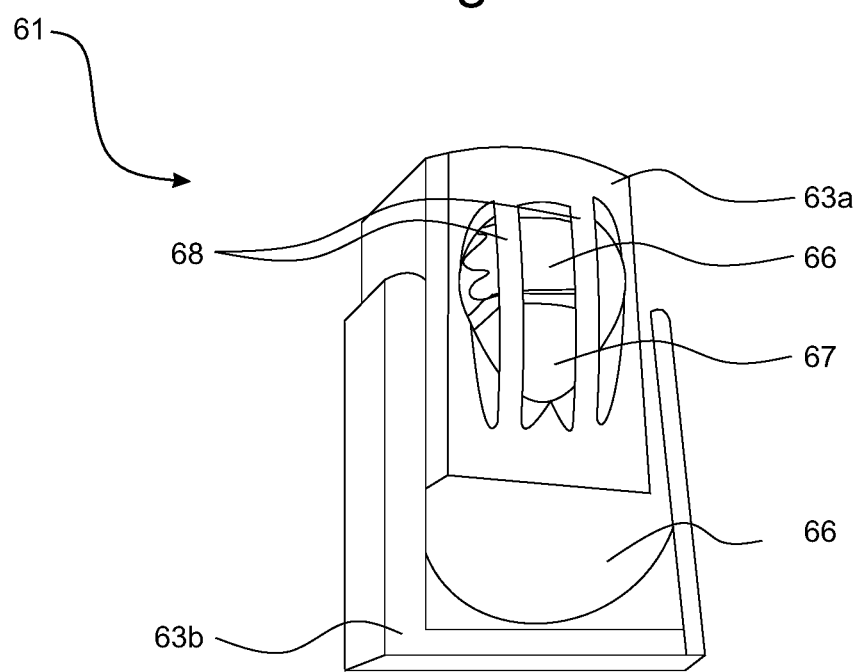

FIG. 8B shows a rear view of the device 61, where a hole is arranged on the back surface of the outer body part 63b. The hole defines a sliding path for sliding the inner body part 63a. The inner body part 63a also comprises a hole on its back surface, wherein the hole is divided by a blocking element 68. The blocking element 68 serves to prevent the limb to enter the hole too far with the risk of becoming entrapped, in particular for preventing finger entrapment.

Figure 9A:
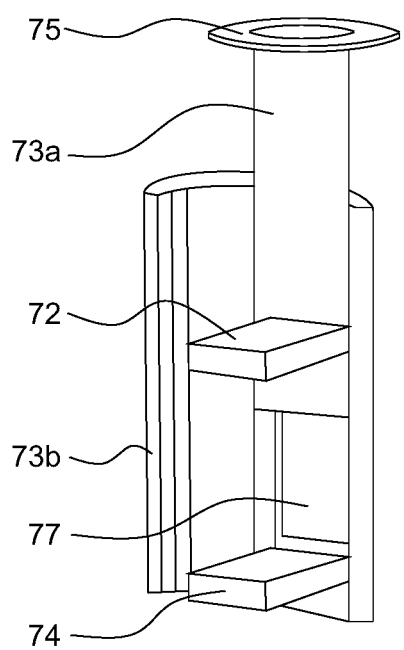
FIGS. 9A and 9B show a seventh embodiment of a device according to the invention.
Figure 9B:
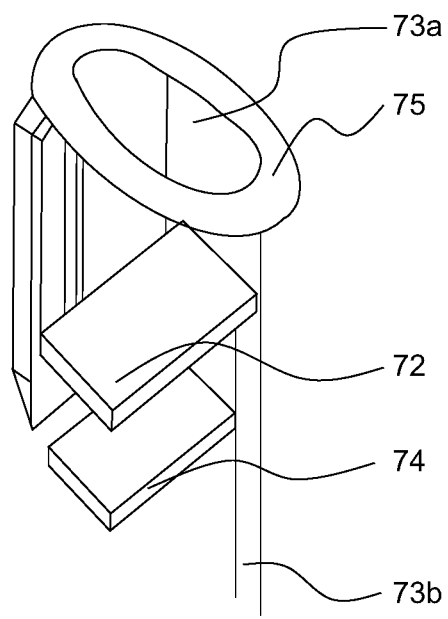

FIG. 9A-B shows a seventh embodiment of the device 71 according to the present invention. Analogously to the device 61 shown in FIG. 8, the device 71 in FIG. 9 comprises a body having a first body part 73a being an inner body part and a second body part 73b being an outer body part, such that the inner body part is slidable along a sliding path of the outer body part formed by a back hole while the two body parts engage each other. In the engaged state shown in FIG. 9A, an opening 77 is formed as overlap between the two holes of the body parts 63a, b.

The inner body part 73a comprises a press element 75 on its top end for pressing the inner body part 73a and an end plate 72 on its bottom end opposite to the press element 75. At the bottom of the outer body part 73b, a bottom plate 74 is arranged for defining a volume for receiving a resetting element and/or a centering element. Preferably, a piece of elastic foam and/or flexible silicon may be used to function as both a resetting element and a centering element, analogously to the embodiment in FIG. 8.

Figure 10A:
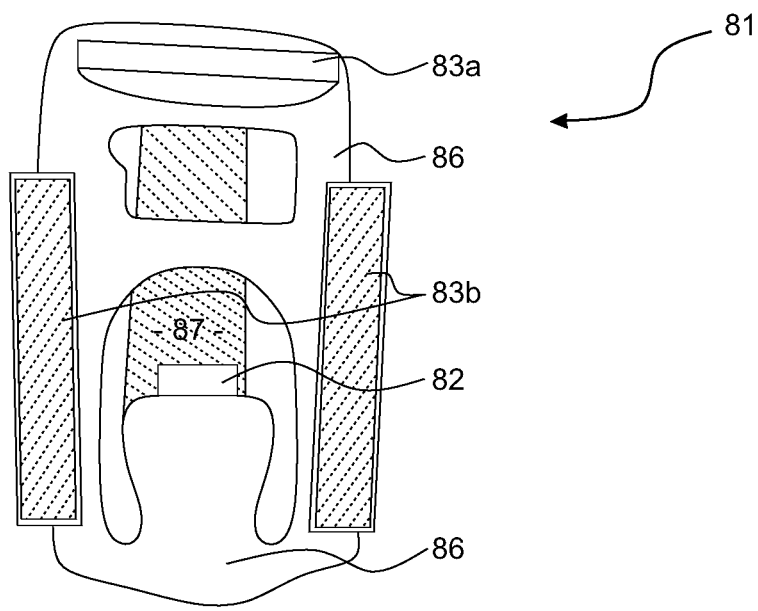
FIGS. 10A and 10B show an eighth embodiment of a device according to the invention.
Figure 10B:
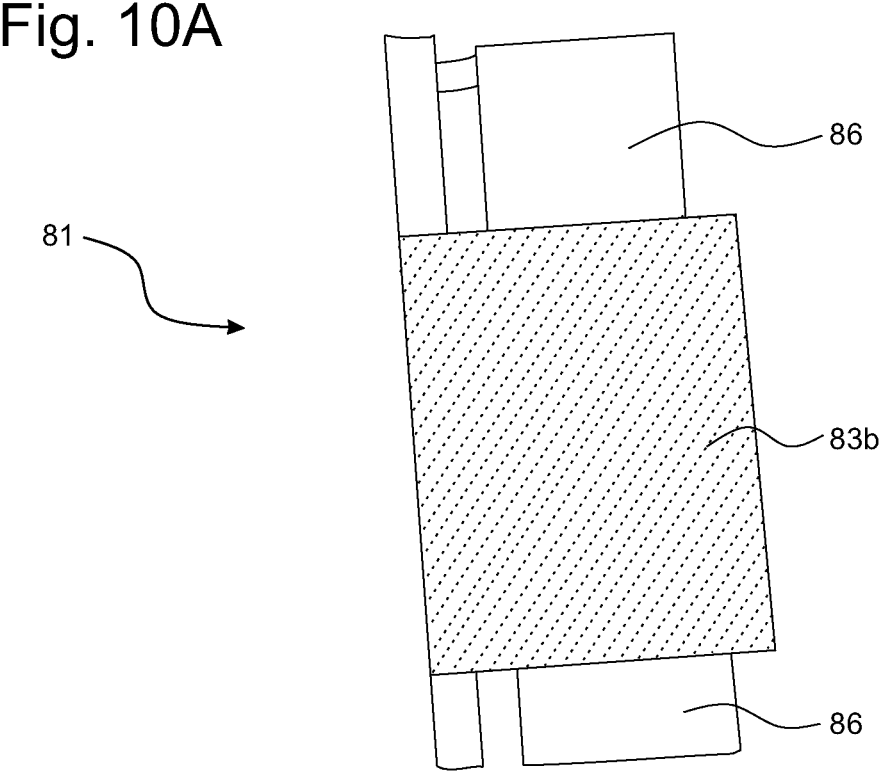

FIG. 10A-B shows an eighth embodiment of the device 81 according to the present invention. FIG. 10A shows a front view and FIG. 10B a side view of the device 81. The device 81 comprises a body having a first body part 83a being an inner body part and a second body part 83b being an outer body part, such that the inner body part is slidable within the outer body part while the two body parts engage each other, analogously to the embodiment shown in FIG. 8. The inner body part 83a comprises an end plate 82 for defining a space for receiving a piece of elastic foam 86.

By pressing the inner body part 83a from top towards the bottom side of the device, the opening 87 for receiving a limb (e.g. a finger) can be adjusted in its size. The opening for receiving the limb is in between 82 and the foam arch slightly above it. As can be seen in FIG. 10, the flexible foam 86 is arranged so that it is surrounded by the device body, in particular within the body.

FIG. 11 shows a ninth embodiment of the device 91 where the flexible foam 96 is arranged so that it at least partially, preferably fully surrounds the device body. In particular, the flexible foam 96 comprises a plurality of holes for receiving the press element 95 of the inner body part 93a and two side elements 99 of the outer body part 93b. In a preferable embodiment, the holes are configured so that they are not visible from outside but just a single piece of foam is visible.

Figure 11A:
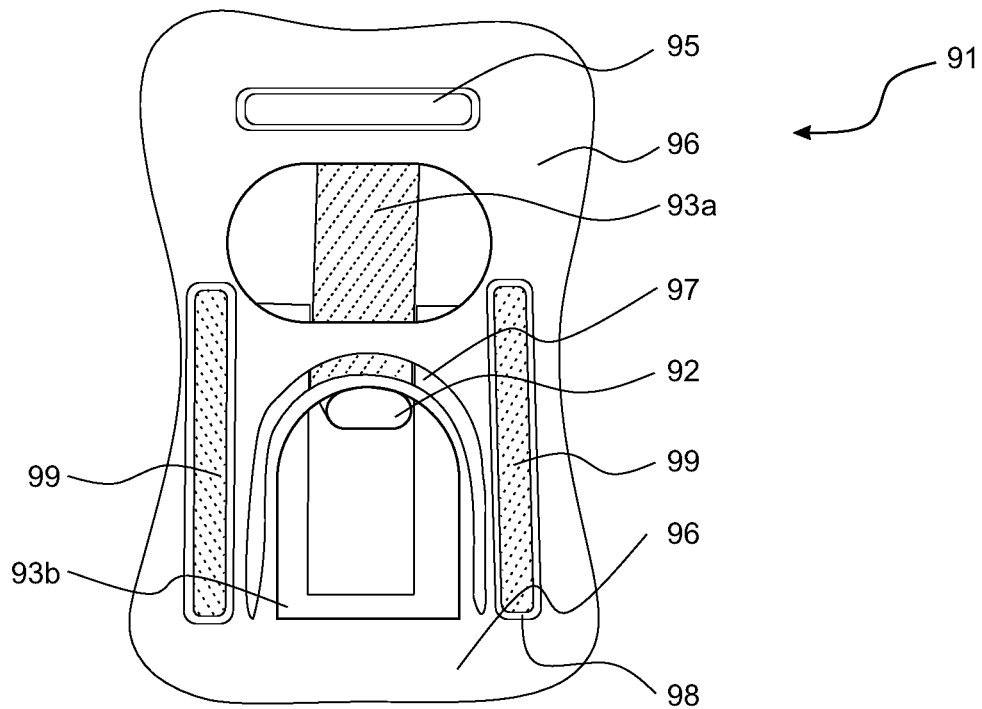
FIGS. 11A and 11B show a ninth embodiment of a device according to the invention.
Figure 11B:
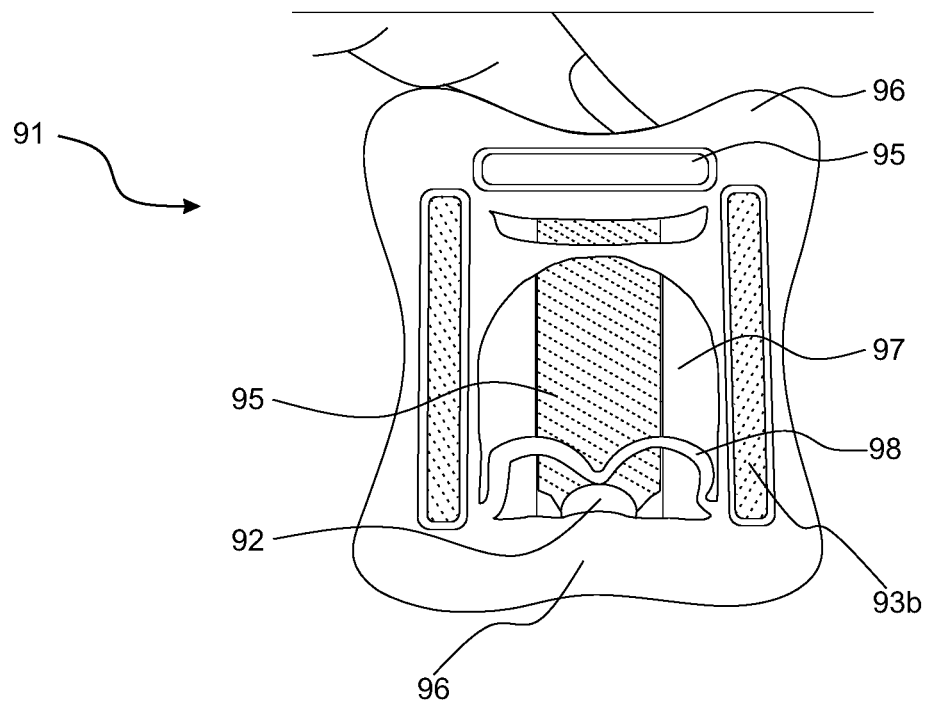

An end element 92 is arranged at the bottom of the inner body part 93a which is connected with a curved stripe 98 of the flexible foam 96 defining the opening 97 from the bottom side. The curved stripe 98 can thus be pulled up and down while sliding the inner body part 93a along the sliding path of the outer body part 93b. In FIG. 11A, the inner body part 93a is pulled substantially out of the outer body part 93b, so that the opening 97 for receiving a limb has a relatively small size. In FIG. 11B, the inner body part 93a is pressed tightly towards the interior of the outer body part 93b so that the opening 97 has a relative large size.

Preferably, the device 71 shown in FIG. 9 serves as the inside of the device 81, 91 shown in FIGS. 10 and 11. Further preferably, the limb-receiving opening is formed by the resetting element (foam or silicon) as shown in FIGS. 10 and 11.

Figure 12A:
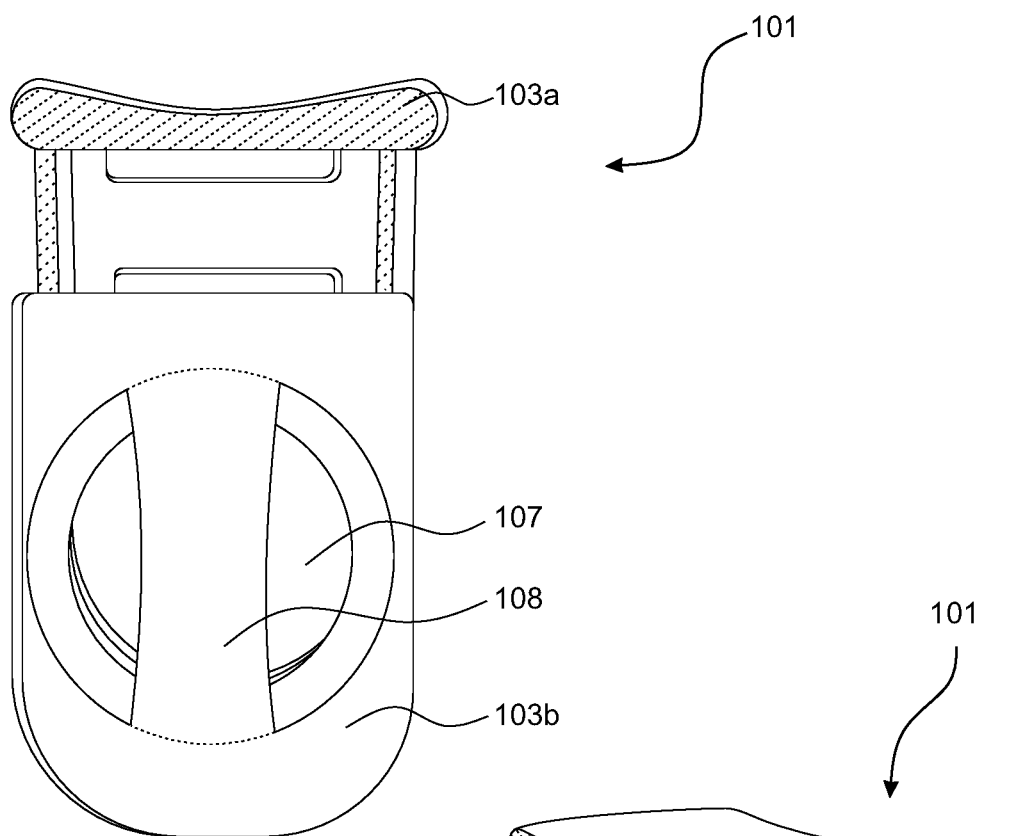
FIGS. 12A and 12B show a tenth embodiment of a device according to the invention.

FIG. 12 shows a tenth embodiment of the device 101 according to the present invention. The device 101 comprises a body having a first body part 103a being an inner body part and a second body part 103b being an outer body part. The inner body part 103a is, analogously to the first embodiment shown in FIG. 1, slidable along a sliding path within the outer body part 103b. The difference between both embodiments is that the device 101 in FIG. 12 comprises a blocking element 108 on a rear side (FIG. 12A) of the outer body part 103b. The blocking element 108 serves as a limitation to the movement of the limb (e.g. a finger) while being receiving by the opening 107 from a side opposite to the rear side shown in FIG. 12A. This prevents the limb, in particular a finger, from penetrating completely through the opening 107, thereby reducing the risk of finger entrapment.

Figure 12B:
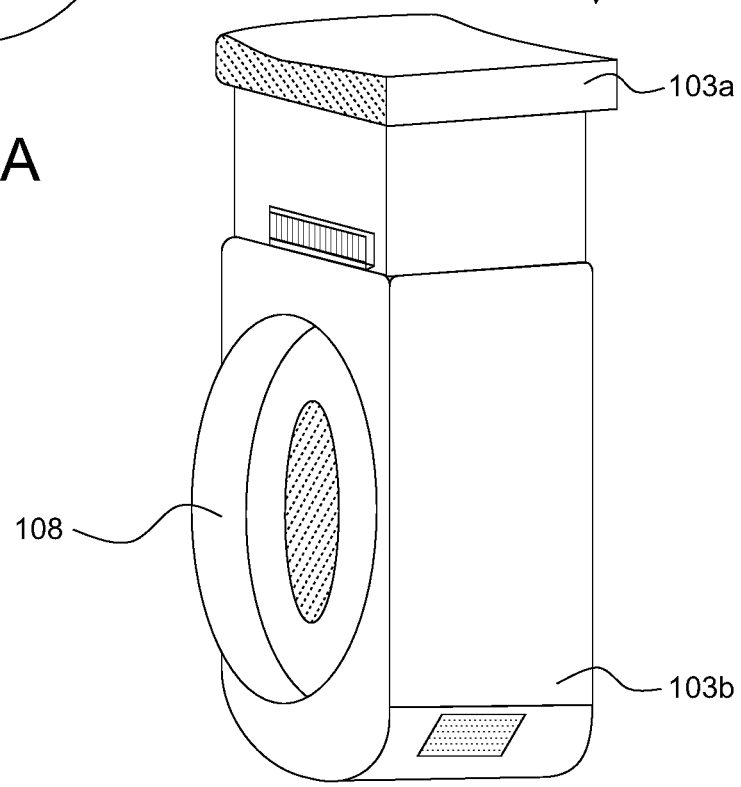

As shown in FIG. 12A-B, the blocking element 108 has exemplarily a curved form, wherein the curvature is preferably convex (i.e. the middle part goes towards the exterior of the outer body part 103b). The depth of the finger that can be received beyond the opening 107 on the front side is determined by the curvature of the blocking element 108. Other forms (e.g. rectangular) may be used by the blocking element 108. Also, the blocking element 108 shown in FIG. 12A-B is made of the same material as the rest of the outer body part 103b. This is, however, not limiting for the present invention since the blocking element 108 may be made of a different material as the rest of the outer body part 103b (e.g. a flexible material such as rubber or silicon).

In an alternative embodiment, the body may comprise a flexible part combining the function of the resetting element and the adjustable opening. This central flexible part can be made of silicone, and it connectable by two rigid (for instance plastic) parts at two opposite side of the body. By compressing these two rigid parts on the body, the body parts of the body move relative to each other such that an opening is defined, thereby allowing the limb, such as a finger, to be received. By releasing the compression force on the body, the body parts move relative to each other in the opposite direction than following compression thereby enclosing the limb. Once enclosed, the physiological parameter measurement, such as measurement (when the body comprises a physiological sensor), can take place. In addition advantages herein mentioned, this embodiment has the additional advantage that the wear and tear of the body, and the body parts is reduced, thereby improved robustness.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A device to measure a physiological parameter of a human limb, comprising:
   a body comprising a first body part and a second body part, which are movable relative to each other to define an opening with an adjustable size to receive the limb therein, and
   a receiving element to receive a physiological sensor to interact with the limb received in the opening,
   wherein, to adjust the size of the opening;
   the first and second body parts are slidable or twistable relative to each other while at least partially engaging or intersecting each other, or the first and second body parts are configured to form a clip having an L-shaped end section to at least partially enclose the limb when received in the opening;
   wherein the device further comprises a centering element to align the limb in the opening of the body relative to the receiving element, wherein the centering element comprises a connecting element arranged to connect between the first and second body parts; and
   wherein the connecting element comprises an elastic sleeve to connect the first body part with the second body part, wherein the elastic sleeve has a predetermined shape to which the elastic sleeve returns after being deformed.

2. The device according to claim 1, wherein the first body part is an inner body part engagingly slidable along a length within the second body part being an outer body part, and/or the second body part comprises a blocking element to limit a receivable depth of the limb.

3. The device according to claim 1, wherein the opening defines a circumference, and the first body part is arranged to intersect with the second body part over at least a part of the circumference of the opening.

4. The device according to claim 1, wherein the second body part comprises two sliding holes to slidably guide the first body part, when two arms of the first body part penetrate the sliding holes.

5. The device according to claim 1, further comprising a resetting element to charge the body parts with a resetting force in order to cause the body parts to be in a reset position relative to each other, and/or the sensor coupled to the body.

6. The device of claim 1 wherein the sensor comprising a light source to generate a measurement light signal and a light detector to detect the measurement light signal after its interaction.

7. The device according to claim 6, wherein the light source is connected to a surface of one of the first and second body parts and the light detector is connected to a surface of the other of the first and second body parts.

8. A method for measuring physiological parameter of a human limb, comprising:
   providing a body comprising a first body part and a second body part, which are movable relative to each other to define an opening with an adjustable size for receiving the limb therein,
   receiving a physiological sensor for interacting with the limb received in the opening,
   adjusting the size of the opening by sliding or twisting the first and second body parts relative to each other while they at least partially engage or intersect each other, or by configuring the first and second body parts to form a clip having an L-shaped end section for at least partially enclosing the limb when received in the opening,
   wherein the method further comprises aligning, using a centering element, the limb in the opening of the body relative to a receiving element, wherein the centering element is provided by a connecting element arranged for connecting between the first and second body parts; and
   wherein the method further comprises connecting, using an elastic sleeve of the connecting element, the first body part with the second body part, wherein the elastic sleeve has a predetermined shape to which the elastic sleeve returns after being deformed.

9. A device to measure a physiological parameter of a human limb, comprising:
   a body comprising a first body part and a second body part, which are movable relative to each other to define an opening with an adjustable size to receive the limb therein, and
   a receiving element to receive a physiological sensor to interact with the limb received in the opening,
   wherein, to adjust the size of the opening:
   the first and second body parts are slidable or twistable relative to each other while at least partially engaging or intersecting each other, or the first and second body parts are configured to form a clip having an L-shaped end section to at least partially enclose the limb when received in the opening; and
   wherein the device further comprises a centering element to align the limb in the opening of the body relative to the receiving element, wherein the centering element comprises a flexible material to fill up at least a part of a space between the limb received in the opening and a side of the opening.

10. The device according to claim 9, wherein the centering element:
   comprises a V-shaped section formed in the first body part.

11. The device according to claim 9, wherein the flexible material is configured to enclose at least a part of the sensor and/or the flexible material comprises foam or silicon.

12. The device according to claim 9, wherein the centering element:
   comprises a diaphragm, which is attached to the first body part being an inner body part engagingly slidable along a length within the second body part being an outer body part; or
   comprises two flexible membranes arranged adjacent to each other to define a slit within the opening.

* * * * *